(12) United States Patent
Chiou et al.

(10) Patent No.: US 10,787,657 B2
(45) Date of Patent: Sep. 29, 2020

(54) METHODS FOR EFFICIENT INTRACELLULAR DELIVERY USING ANISOTROPIC MAGNETIC PARTICLES

(71) Applicant: The Regents of the University of California, Oakland, CA (US)

(72) Inventors: Pei-Yu E. Chiou, Los Angeles, CA (US); Michael A. Teitell, Tarzana, CA (US); Ming-Yu Lin, Hsinchu County (TW); Yi-Chien Wu, Taichung (TW); Jessica Zhou, Chino, CA (US)

(73) Assignee: The Regents of the University of California, Oakland, CA (US)

( * ) Notice: Subject to any disclaimer, the term of this patent is extended or adjusted under 35 U.S.C. 154(b) by 289 days.

(21) Appl. No.: 15/387,230

(22) Filed: Dec. 21, 2016

(65) Prior Publication Data

US 2017/0175102 A1 Jun. 22, 2017

Related U.S. Application Data

(60) Provisional application No. 62/270,372, filed on Dec. 21, 2015.

(51) Int. Cl.
| | | |
|---|---|---|
| *B82Y 5/00* | (2011.01) | |
| *C12N 13/00* | (2006.01) | |
| *C12N 15/87* | (2006.01) | |
| *C12N 15/89* | (2006.01) | |

(52) U.S. Cl.
CPC ........... *C12N 13/00* (2013.01); *C12N 15/895* (2013.01)

(58) Field of Classification Search
None
See application file for complete search history.

(56) References Cited

U.S. PATENT DOCUMENTS

| | | | | |
|---|---|---|---|---|
| 2008/0006281 A1* | 1/2008 | Sih | ........................ | A61M 37/00 128/899 |
| 2008/0075701 A1 | 3/2008 | Hong et al. | | |
| 2010/0221346 A1* | 9/2010 | Plank | ..................... | C12N 15/87 424/489 |
| 2012/0253102 A1* | 10/2012 | Marban | ............. | A61M 25/0068 600/12 |

OTHER PUBLICATIONS

Lin et al., 2015 Transducers-2015 18th International Conference on Solid-State Sensors, Actuators and Microsystems (Transducers) IEEE, 2015 (Year: 2015).*
Shen et al., Chemistry of Materials 2012, 24, 1, 230-235 (Year: 2012).*
Bae et al. (2011) "Surface functionalized hollow manganese oxide nanoparticles for cancer targeted siRNA delivery and magnetic resonance imaging." *Biomaterials* 32: 176-184.
Boukany et al. (2011) "Nanochannel electroporation delivers precise amounts of biomolecules into living cells." *Nat. Nanotechnol.*, 6(11): 747-754 DOI: 10.1038/NNANO.2011.164.
Colombo et al. (2012) "Biological applications of magnetic nanoparticles" *Chem. Soc. Rev.* 41(11): 4306-4334.
Dobson J (2006) "Gene therapy progress and prospects: magnetic nanoparticle-based gene delivery." *Gene Therapy* 13: 283-287.
Gu et al. (2010) "Transfection of Pig Somatic Cells using Magnetic nanoparticle as Gene Carrier." *European Cells and Materials* 20(3): 294-294.
Johannsen et al. (2006) "Thermotherapy using magnetic nanoparticles combined with external radiation in an orthotopic rat model of prostate cancer." *The Prostate* 66: 97-104.
Na et al. (2013) "Probing Enzymatic Activity inside Living Cells Using a Nanowire-Cell "Sandwich" Assay" *Nano Lett.*, 13(1): 153-158 [NIH Public Access—Author Manuscript—11 pages].
Pankhurst et al. (2003) "Applications of magnetic nanoparticles in biomedicine." *J Phys D: Appl Phys* 36: R167-R181.
Plank et al. (2003). "Enhancing and targeting nucleic acid delivery by magnetic force" *Expert opinion on biological therapy*. 3(5): 745-58.
Plank et al. (2003) "The magnetofection method: using magnetic force to enhance gene delivery." *Biol Chem* 384(5): 737-747.
Plank, et al. (2011). "Magnetically enhanced nucleic acid delivery. Ten years of magnetofection-progress and prospects". *Advanced Drug Delivery Reviews* 63(14-15): 1300-1331.
Salem et al. (2003) "Multifunctional nanorods for gene delivery." *Nat Mater* 2: 668-671.
Scherer et al. (2002). "Magnetofection: enhancing and targeting gene delivery by magnetic force in vitro and in vivo". *Gene Therapy* 9(2): 102-109.
Singh et al. (2013) "Comparative study of genotoxicity and tissue distribution of nano and micron sized iron oxide in rats after acute oral treatment" *Toxicol. Appl. Pharmacol.*, 266(1): 56-66.
Wang et al. (2014) "A Magnetic Nanoparticle-Based Multiple-Gene Delivery System for Transfection of Porcine Kidney Cells." *PLoS One* 9(7): e102886 (9 pages) https://doi.org/10.1371/journal.pone.0102886.
Wu et al. (2011) "Photothermal Nanoblade for Large Cargo Delivery into Mammalian Cells" *Anal. Chem.*, 83(4): 1321-1327 [NIH Public Access—Author Manuscript—13 pages] doi:10.1021/ac102532w.
Wu et al. (2015) "Massively Parallel Delivery of Large-Sized Cargo into Mammalian Cells with Light Pulses" *Nat. Meth.* 12(5): 439-444 [HHS Public Access—Author manuscript—19 pages].

* cited by examiner

*Primary Examiner* — James D Schultz
(74) *Attorney, Agent, or Firm* — Tom Hunter; Weaver Austin Villeneuve & Sampson LLP

(57) ABSTRACT

In various embodiments methods are provided for delivering an agent of interest (e.g., protein, antibody, nucleic acid) into cells. In certain embodiments the method comprises contacting the cells with anisotropic magnetic particles in the presence of the agent; and applying a substantially uniform magnetic field to said magnetic particles where movement of said particles induced by said magnetic field introduces transient openings into said cell facilitating entry of said agent of interest into said cells.

28 Claims, 15 Drawing Sheets

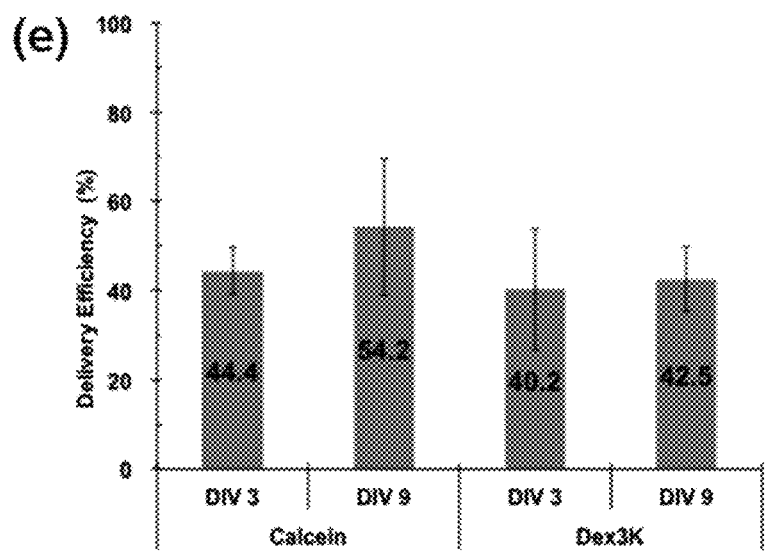
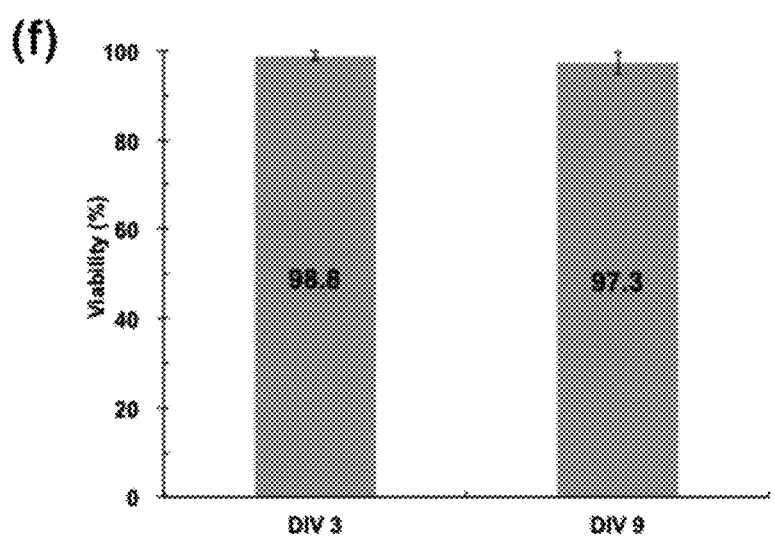
*Fig. 7, cont'd.*

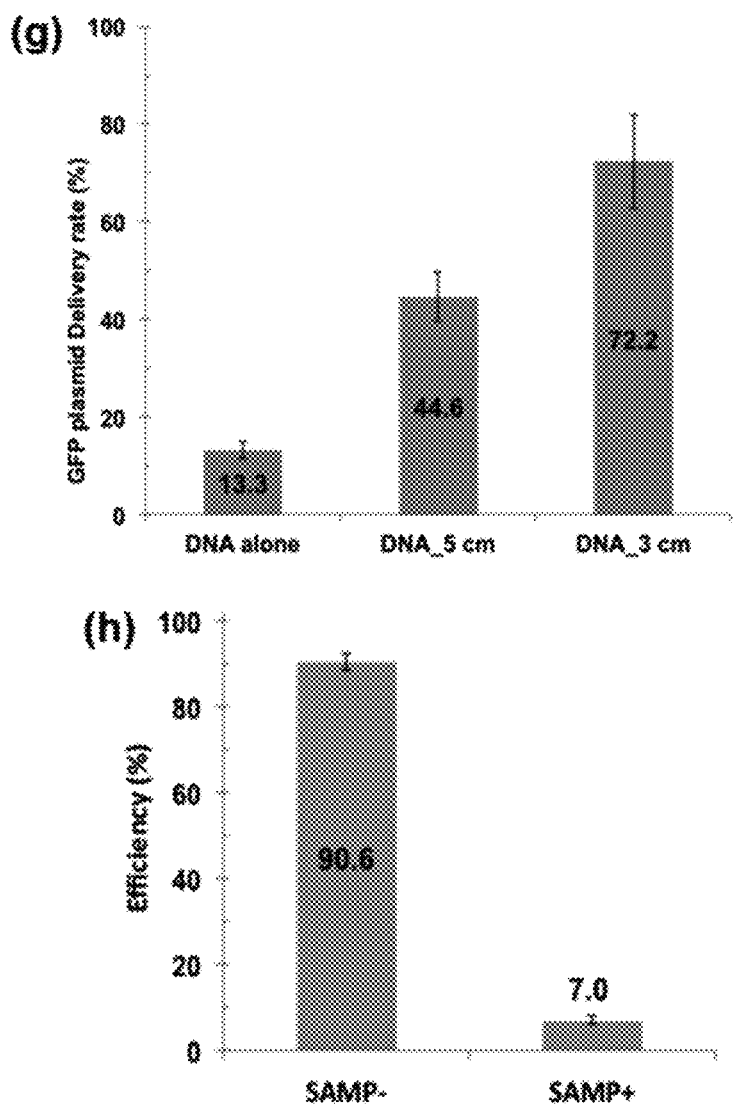
Fig. 8, cont'd.

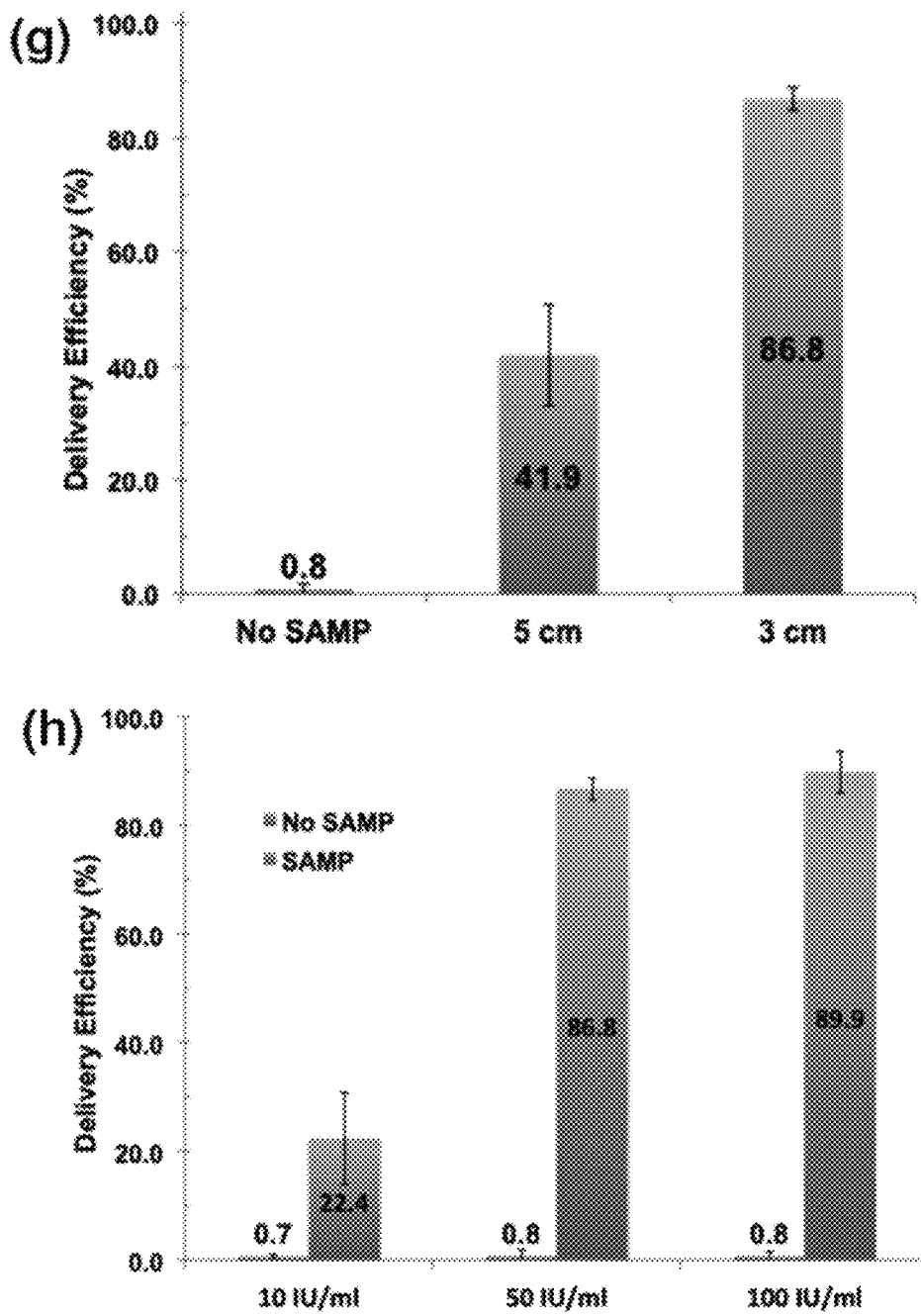
*Fig. 9, cont'd.*

METHODS FOR EFFICIENT INTRACELLULAR DELIVERY USING ANISOTROPIC MAGNETIC PARTICLES

CROSS-REFERENCE TO RELATED APPLICATIONS

This application claims benefit of and priority to U.S. Ser. No. 62/270,372, filed on Dec. 21, 2015 which is incorporated herein by reference in its entirety for all purposes.

STATEMENT OF GOVERNMENTAL SUPPORT

[Not Applicable]

BACKGROUND

Efficient delivery of exogenous functional molecules into cells is required in numerous biomedical applications. For example, intracellular delivery of enzymes is a very promising therapeutic approach for genetic diseases because of their catalytic activity and specificity (Estrada et al. (2014) *J. Pharm. Sci.* 103(6): 1863-1871; Chang et al. 92014) *Small*, 10(22): 4785-4795). DNA and RNA transfection is indispensible for fundamental biology studies (Luo and Saltzman (2000) *Nat. Biotechnol.*, 18(1): 33-37; Dahlman et al. (2014) *Nat. Nanotechnol.*, 9(8): 648-655) and gene therapy (Forbes and Peppas (2014) *ACS Nano*, 8(3): 2908-2917; Shen et al. (2015) *J. Visualized Exp.*, 2015(95): e52075-e75; Yin et al. (2014) *Nat. Rev. Genet.* 15(8): 541-555). Delivery of functional nanoparticles such as antibody-conjugated quantum dots enables intracellular labeling and imaging (Xu et al. (2012) *Nano Lett.* 12(11): 5669-5672).

Current delivery approaches are versatile and each has it own unique advantages and limitations. For example, viral-based approaches can provide high transfer efficiency but are restricted to kb-sized nucleic acids with potential immunologic concerns (Dobrovolskaia and McNeil (2015) *Expert Opin. Drug Delivery*, 12(7): 1163-1175; Liu and Wang (2015) *Expert Opin. Biol. Ther.* 15(4): 559-567). Chemical methods that utilize lipids, cationic polymers, or insoluble precipitates vary in delivery efficiency, and are highly cell type dependent (Movahedi et al. (2015) *Nanomedicine: NBM*, 11(6/): 1575-1584; Deng et al. (2014) *Biomaterials*, 35(18): 5006-5015). Physical approaches, such as electroporation, optoporation, and magnetofection have been developed. However, cell viability, efficiency, setup cost, conjugation of molecules onto magnetic nanoparticles, and cytotoxicity from iron oxide nanoparticles are current obstacles (Boukany et al. (2011) *Nat. Nanotechnol.*, 6(11): 747-754; Na et al. (2012) *Nano Lett.*, 13(1): 153-158; Singh et al. (2013) *Toxicol. Appl. Pharmacol.*, 266(1): 56-66; Colombo et al. (2012) *Chem. Soc. Rev.* 41(11): 4306-4334; Wu et al. (2011) *Anal. Chem.*, 83: 1321-1327; Wu et al. (2015) *Nat. Meth.* 12: 439-444).

SUMMARY

Here, we demonstrate a novel, low cost, easy-to-implement, and high-throughput platform called SAMP (shape-anisotropic magnetic particles) for macromolecule delivery into a broad range of mammalian cell types, including, but not limited to stem cells, primary human dermal fibroblasts (NHDFs), and mouse cortical neurons that are difficult to transfect.

Various embodiments contemplated herein may include, but need not be limited to, one or more of the following:

Embodiment 1

A method of delivering an agent of interest into cells, said method comprising:
  contacting said cells with anisotropic magnetic particles in the presence of said agent;
  applying a substantially uniform magnetic field to said magnetic particles where movement of said particles induced by said magnetic field introduces transient openings into said cell facilitating entry of said agent of interest into said cells.

Embodiment 2

The method of embodiment 1, wherein said substantially uniform magnetic field is created by a magnet disposed in proximity to said cells.

Embodiment 3

The method of embodiment 2, wherein said magnet comprises a magnet selected from the group consisting of a neodymium magnet, a samarium cobalt (SmCo) magnet, an alnico magnet, and a ceramic or ferrite magnet.

Embodiment 4

The method of embodiment 3, wherein said magnet comprises a neodymium magnet.

Embodiment 5

The method according to any one of embodiments 2-4, wherein said cells are disposed in a vessel and said applying a substantially uniform magnetic field comprises disposing said vessel over said magnet.

Embodiment 6

The method according to any one of embodiments 2-5, wherein said magnet ranges in size from about 0.5 inch in length or diameter up to about 6 inches in length or diameter.

Embodiment 7

The method according to any one of embodiments 2-6, wherein said magnet has surface field strength that ranges from about 0.001 Tesla up to about 10 Tesla.

Embodiment 8

The method according to any one of embodiments 2-7, wherein said magnet is disposed to provide a field strength at said cells ranging from about 0.01 tesla up to about 0.1 tesla.

Embodiment 9

The method of embodiment 1, wherein said substantially uniform magnetic field is created by an electromagnet disposed in proximity to said cells.

Embodiment 10

The method of embodiment 9, wherein said cells are disposed in a vessel and said applying a substantially uniform magnetic field comprises disposing said vessel over said electromagnet.

Embodiment 11

The method of embodiments 5 or 10, wherein said vessel comprises a vessel selected from the group consisting of a cell culture vessel, and a well in a microtiter plate.

Embodiment 12

The method according to any one of embodiments 1-11, wherein said substantially uniform magnetic field is applied for a period of time ranging from about 0.5 sec up to about 30 sec.

Embodiment 13

The method of embodiment 12, wherein said substantially uniform magnetic field is applied for about 1 second.

Embodiment 14

The method according to any one of embodiments 1-13, wherein said further comprises using a magnet to remove said magnetic particles from a medium in which said cells are disposed.

Embodiment 15

The method of embodiment 14, wherein the magnet used to remove said magnetic particles is not the magnet used to apply said substantially uniform magnetic field.

Embodiment 16

The method of embodiment 14, wherein the magnet used to remove said magnetic particles is the same magnet used to apply said substantially uniform magnetic field.

Embodiment 17

The method according to any one of embodiments 14-16, wherein said cells are cultured in the presence of said agent of interest for a period of time after removal of said magnetic particles.

Embodiment 18

The method of embodiment 17, wherein said period of time ranges up to about 4 hours, or up to about 2 hours, or up to about 1 hour, or up to about ½ hour, or up to about ¼ hour, or up to about 10 minutes, or up to about 5 minutes, or up to about 1 minute.

Embodiment 19

The method according to any one of embodiments 1-18, wherein said anisotropic magnetic particles comprise a material selected from the group consisting of nickel, nickel, and cobalt, and alloys thereof.

Embodiment 20

The method according to any one of embodiments 1-19, wherein said anisotropic magnetic particles range in average or median size from about 20 µm, or from about 30 µm, or from about 40 µm, or from about 50 µm in up to about 200 µm, or up to about 150 µm, or up to about 100 µm, or up to about 80 µm, or up to about 60 µm.

Embodiment 21

The method according to any one of embodiments 1-20, wherein said magnetic particles are of a size that prevents internalization into said cells.

Embodiment 22

The method according to any one of embodiments 1-21, wherein said magnetic particles are of a size that prevents internalization into said cells via endocytosis, or pinocytosis.

Embodiment 23

The method according to any one of embodiments 1-22, wherein said magnetic particles are sterile before application to said cells.

Embodiment 24

The method according to any one of embodiments 1-23, wherein said magnetic particles are disposed in a flexible membrane that is applied to said cells.

Embodiment 25

The method of embodiment 24, wherein said flexible membrane comprise PDS or another material used in soft lithography.

Embodiment 26

The method according to any one of embodiments 1-25, wherein said magnetic particles are applied to said cells at a density ranging from about $1 \times 10^3$ particles/cm, or about $5 \times 10^3$ particles/cm, or from about $1 \times 10^4$ particles/cm, or from about $4 \times 10^4$ particles/cm, or from about $6 \times 10^4$ particles/cm up to about $3 \times 10^6$ particles/cm, or up to about $1 \times 10^6$ particles/cm, or up to about $5 \times 10^5$ particles/cm, or up to about $5 \times 10^4$ particles/cm.

Embodiment 27

The method according to any one of embodiments 1-26, wherein said agent of interest comprises one or more agents selected from the group consisting of a nucleic acid and a protein or peptide.

Embodiment 28

The method according to any one of embodiments 1-26, wherein said agent of interest comprises one or more agents selected from the group consisting of an enzyme, a plasmid, a viral vector, a cosmid, an artificial chromosome, an antibody, an RNAi, and components of a CRISPR/Cas9 system (e.g., Cas9, and/or crRNA, and/or trRNA), color dyes of different sizes, calcium and other small molecules.

Embodiment 29

The method of embodiment 28, wherein said agent of interest is selected from the group consisting of Cas9 from Streptococcus pyogenes (SpCas9) or a nucleic acid encoding Cas9 from Streptococcus pyogenes (SpCas9), Cas9 from Streptococcus aureus (SaCas9) or a nucleic acid encoding, Cas9 from Streptococcus aureus (SaCas9), a Cpf1 nuclease or a nucleic acid encoding the Cpf1 nuclease, a vector (e.g., an AAV vector or lentiviral vector) encoding a Cas9 (e.g., SpCas9, SaCas9, etc.) and a single guide RNA or two guide RNAs, and a vector (e.g., an AAV vector or lentiviral vector) encoding a Cpf1 (e.g., AsCpf1, LbCpf1) and a single guide RNA.

Embodiment 30

The method according to any one of embodiments 1-29, wherein said cells are prokaryotic cells.

Embodiment 31

The method according to any one of embodiments 1-29, wherein said cells comprise eukaryotic cells.

Embodiment 32

The method of embodiment 31, wherein said cells comprise mammalian cells.

Embodiment 33

The method of embodiment 32, wherein said cells comprises human cells.

Embodiment 34

The method according to any one of embodiments 32-33, wherein said cells comprise cells selected from the group consisting of fibroblasts, neural cells (e.g., cortical neurons), A549 cells, HeLa cells CHO cells primary human mammary epithelial cells (HMEC), red blood cells, white blood cells (including T cells and B cells), and stem cells.

Embodiment 35

The method of embodiment 34, wherein said cells comprise stem cells selected from the group consisting of fetal stem cells, adult stem cells, cord blood stem cells, and induced pluripotent stem cells.

Embodiment 36

The method of embodiment 34, wherein said cells comprise stem cells derived from bone marrow or adipose tissue.

Embodiment 37

The method according to any one of embodiments 1-36, wherein said method is configured for a high throughput format.

Embodiment 38

The method of embodiment 37, wherein said method is configured to perform at least 2, or at least 4, or at least 8, or at least 16, or at least 32, or at least 64, or at least 128 different transfections simultaneously.

Embodiment 39

The method according to any one of embodiments 1-38, wherein said substantially uniform magnetic field is not provided by a component of a magnetic stirrer.

Embodiment 40

The method according to any one of embodiments 1-38, wherein said substantially uniform magnetic field is not provided as an element of a magnetic cell isolation or cell component isolation.

Embodiment 41

A kit for the transfection of cells, said kit comprising:
a container containing anisotropic magnetic particles; and
a magnet.

Embodiment 42

The kit of embodiment 41, wherein said magnet has a substantially uniform magnetic field sufficient to induce movement of said particles and to introduce transient openings into a cell in contact with said particles and to facilitating entry of an agent of interest into said cell.

Embodiment 43

A kit for the transfection of cells, said kit comprising a cell culture vessel containing anisotropic magnetic particles, said cell culture vessel provides an aliquot of said magnetic particles containing sufficient particles for a single transfection procedure.

Embodiment 44

A kit for the transfection of cells, said kit comprising a plurality of containers each containing anisotropic magnetic particles, wherein each container provides an aliquot of said magnetic particles sufficient for a single transfection procedure.

Embodiment 45

The kit of embodiment 44, wherein each container provides sufficient magnetic particles to apply said particles to said cells at a density ranging from about $1 \times 10^3$ particles/cm, or from about $5 \times 10^3$ particles/cm, or from about $1 \times 10^4$ particles/cm, or from about $2 \times 10^4$ particles/cm, or from about $4 \times 10^4$ particles/cm, or from about $6 \times 10^4$ particles/cm up to about $1 \times 10^5$ particles/cm, or up to about $5 \times 10^5$ particles/cm, or up to about $1 \times 10^6$ particles/cm, when said cells are disposed on a substrate of about 1 cm$^2$ up to about 25 cm$^2$.

Embodiment 46

The kit according to any one of embodiments 44-45, wherein said kit further comprises a magnet that provides a substantially uniform magnetic field sufficient to induce movement of said particles and to introduce transient openings into a cell in contact with said particles and to facilitating entry of an agent of interest into said cell.

Embodiment 47

The kit according to any one of embodiments 41-46, wherein said kit further contains instruction materials teaching a transfection method according to any one of embodiments 1-38.

Embodiment 48

The kit according to any one of embodiments 41-47, wherein said kit further comprises a vessel for holding cells for transfection.

Embodiment 49

The kit according to any one of embodiments 41-48, wherein said anisotropic magnetic particles comprise a material selected from the group consisting of iron, nickel, cobalt, and alloys thereof.

Embodiment 50

The kit according to any one of embodiments 41-49, wherein said anisotropic magnetic particles range in average or median size from about 20 μm, or from about 30 μm, or from about 40 μm, or from about 50 μm in diameter up to about 200 μm, or up to about 150 μm, or up to about 100 μm, or up to about 80 μm, or up to about 60 μm in diameter.

Embodiment 51

The kit according to any one of embodiments 41-50, wherein said magnetic particles are of a size that prevents internalization into said cells.

Embodiment 52

The kit according to any one of embodiments 41-51, wherein said magnetic particles are of a size that prevents internalization into said cells via endocytosis, or pinocytosis.

Embodiment 53

The kit according to any one of embodiments 41-52, wherein said magnetic particles are sterile.

Embodiment 54

The kit according to any one of embodiments 41-53, wherein said magnetic particles are disposed on or in a flexible membrane.

Embodiment 55

The kit of embodiment 54, wherein said flexible membrane comprise PDMS or other material used in soft lithography.

Embodiment 56

The kit according to any one of embodiments 41-55, wherein said magnet comprises a magnet selected from the group consisting of a neodymium magnet, a samarium cobalt (SmCo) magnet, an alnico magnet, and a ceramic or ferrite magnet.

Embodiment 57

The method of embodiment 56, wherein said magnet comprises a neodymium magnet.

Embodiment 58

The kit according to any one of embodiments 41-56, wherein said magnet ranges in size from about 0.5 inch in length or diameter up to about 6 inches in length or diameter.

Embodiment 59

The kit according to any one of embodiments 41-57, wherein said magnet has surface field strength that ranges from about 0.001 Tesla up to about 10 Tesla.

Embodiment 60

The kit according to any one of embodiments 41-59, wherein said magnet provides a field strength ranging from about 0.01 tesla up to about 0.1 tesla.

Embodiment 61

A composition comprising a plurality of anisotropic magnetic particles disposed on or in a surface of a flexible membrane.

Embodiment 62

The composition of embodiment 61, wherein said anisotropic magnetic particles comprise a material selected from the group consisting of nickel, nickel, and cobalt, and alloys thereof.

Embodiment 63

The composition according to any one of embodiments 61-62, wherein said anisotropic magnetic particles range in average or median size from about 20 μm, or from about 30 μm, or from about 40 μm, or from about 50 μm in up to about 200 μm, or up to about 150 μm, or up to about 100 μm, or up to about 80 μm, or up to about 60 μm.

Embodiment 64

The method according to any one of embodiments 61-62, wherein said magnetic particles are of a size that prevents internalization into cells when said particles are contacted to said cells.

Embodiment 65

The composition according to any one of embodiments 61-62, wherein said magnetic particles are of a size that prevents internalization into cells via endocytosis, or pinocytosis when said particle are contacted to said cells.

Embodiment 66

The composition according to any one of embodiments 61-65, wherein said magnetic particles are sterile before application to cells.

Embodiment 67

The composition according to any one of embodiments 61-66, wherein said flexible membrane comprise PDS or another material used in soft lithography.

Embodiment 68

The composition according to any one of embodiments 61-67, wherein said magnetic particles are disposed on said membrane at a density ranging from about $1\times10^3$ particles/cm, or about $5\times10^3$ particles/cm, or from about $1\times10^4$ particles/cm, or from about $4\times10^4$ particles/cm, or from about $6\times10^4$ particles/cm up to about $3\times10^6$ particles/cm, or up to about $1\times10^6$ particles/cm, or up to about $5\times10^5$ particles/cm, or up to about $5\times10^4$ particles/cm.

Embodiment 69

A device for transfecting a cell, said device comprising:
a first channel configured to pass cells in a fluid medium; and
a magnet disposed in sufficient proximity to said first channel so that when said cells, magnetic particles and an agent to be transfected into said cell are disposed in said channel said cells are transfected with said agent.

Embodiment 70

The device of embodiment 69, wherein said device further comprises a second magnet configured to remove magnetic particles from cells or from a fluid stream in said first channel.

Embodiment 71

The device according to any one of embodiments 69-70, wherein said device comprises a second channel or a port configured to deliver magnetic particles into said first channel.

Embodiment 72

The device according to any one of embodiments 69-71, wherein said device is configured to perform a method according to any one of embodiments 1-40.

BRIEF DESCRIPTION OF THE DRAWINGS

FIG. 4A: Numerically simulatied magnetic flux density and field direction in a cross-sectional view using COMSOL, a finite element method. The direction and length of arrows indicate the direction and strength of the magnetic field. FIGS. 4B, 4C: The distribution of magnetic flux density at 3 and 5 cm, respectively, above the surface of the magnet disc.

FIG. 5, panels d-f, show the corresponding bright field images of panels a-c. Scale bar: 200 µm. FIG. 5, panels g, h, show the delivery efficiency and cell viability after SAMP delivery of calcein dye, dextran 3K (panel g), and dextran 40K (panel h) into HeLa cells. The control group is performed by 0.1 mg/ml calcein delivery without SAMP treatment. The data are presented as a ratio of the percentage of delivered cells (cell counts in fluorescence images/cell counts in bright field images) with a total of 517 cells (control), 603 cells (calcein), 1262 cells (dextran 3K), and 525 cells (dextran 40K) from three independent repeat experiments.

FIG. 6, panels d-f, show corresponding bright field images are shown. Scale bar: 200 µm. FIG. 6, panels g, h, show the delivery efficiency (panel g) and cell viability (panel h) after delivery into NHDF cells. The data are presented as a ratio of the percentage of delivered cells (cell counts in fluorescence images/cell counts in bright field images) with a total of 1600 cells (control), 1304 cells (calcein), 650 cells (dextran 3K), and 1052 cells (dextran 40K) from three independent repeat experiments.

FIG. 7, panels b and d show fluorescence and bright field images of mouse cortical neurons (9 DIV) delivered with dextran 3K (1 mg/ml). Scale bar: 100 µm. FIG. 7, panel e, shows delivery efficiency of calcein dye and dextran 3K into neurons on DIV 3 and 9 with SAMP treatment, respectively. FIG. 7, panel f, shows neuron viability on DIV 3 and DIV 9 after SAMP delivery. The data are presented as a ratio of the percentage of delivered cells (cell counts in fluorescence images/cell counts in bright field images) with a total of 710 cells for Calcein-DIV3, 662 cells for Dex3K-DIV3, 1140 cells for Calcein-DIV9, 1017 cells for Dex3K-DIV9, 1447 cells for Viability-DIV3, and 1140 cells for Viability-DIV9.

FIG. 8, panel a) A fluorescence image of GFP expressed-NHDF cells after SAMP delivery. The distance of Ni powders and bottom magnet is 3 cm. The GFP plasmid (6 ng/µl) is pretreated with lipofectamine. Scale bar: 200 µm. FIG. 8, panel b) The control group of GFP expressed-NHDF cells incubated with Lipofectamine-pretreated GFP plasmid without SAMP assisted delivery. Scale bar: 200 μm. FIG. 8, panel c) A fluorescence image of Lamin A/C siRNA delivered-HeLa cells with SAMP. The distance between the Ni powders and the bottom magnet is 3 cm. The Lamin A/C siRNA (50 nM) is pretreated with lipofectamine and labeled with fluorescence dye, DY-547. FIG. 8, panel d) The control group of HeLa cells incubated with Lipofectamine-pretreated Lamin A/C siRNA. FIG. 8, panel e) A fluorescence image of immunocytochemistry staining with Lamin A/C monoclonal antibody on HeLa cells after SAMP delivery of Lamin A/C siRNA. FIG. 8, panel f) Fluorescence immunochemistry staining of Hela cells without SAMP assisted delivery of Lamin A/C. Cells after SAMP delivery of Lamin A/C siRNA shows much weaker fluorescence signals due to the silencing of the expression of Lamin protein by siRNA. FIG. 8, panel g) Comparison of delivery efficiency of SAMP delivery of GFP plasmid into NHDF cells with the magnet disc positioned at 5 cm, 3 cm, away from the cells, and the case without SAMP. FIG. 8, panel h) Comparison of percentage of HeLa cells expressing Lamin A/C protein after delivery of siRNA molecules with SAMP treatment (SAMP+) and without SAMP (SAMP−). For cells after SAMP delivery of siRNA, the expression of Lamin A/C protein is significantly suppressed to 7%.

FIG. 9, panels a, d) SAMP delivery of β-lactamase at 50 IU/ml with the magnet disc at 3 cm. CCF4 (green fluorescence) are generated by cytosolic esterase in NHDF cells. If exogenous β-lactamase was successfully delivered with catalytic functions preserved, it cleaves the CCF4 molecule and generates blue fluorescence. The fluorescence images are taken at 4 hours after delivery. Scale bar: 200 μm. FIG. 9, panels b, e) SAMP delivery of β-lactamase at 10 IU/ml with the magnet disc at 3 cm. FIG. 9, panels c, f) 50 IU/ml of β-lactamase without SAMP treatment. FIG. 9, panels g) Study of the effect of magnetic field strength and the delivery efficiency of β-lactamase (50 IU/ml). Cell viabilities in this study are all above 98%. FIG. 9, panel h) Concentration effect on delivery efficiency using SAMP and without. Higher delivered efficiency is observed with increasing the concentration of β-lactamase. However, without SAMP, the β-lactamase delivery is low even at high concentration.

DETAILED DESCRIPTION

In various embodiments methods of delivering an agent into a cell (transfecting a cell) are provided that utilize shape anisotropic magnetic microparticles (SAMPs). The shape anisotropic magnetic microparticle (SAMP) system provides a method for fast delivery of various molecules into living cells by passage through transient "wounds" introduced on the cell membrane. As illustrated schematically in FIG. 1, a uniform magnetic field magnetizes SAMPs and causes rotation/reorientation of the anisotropic (either shape or crystalline orientation) microparticles to align their axes with the applied field. Cells touching SAMPs are "scratched" which generates a minor lesion on the cell membrane that permits entry of agents that are to be delivered into the cell. The lesions introduced into the cell membrane using the methods described herein are transient and appear to readily close/"heal". The methods can be performed while maintaining cells in a standard incubator environment.

The physically transient lesions on the cell membrane provide penetration pores for molecules of various sizes to be delivered into the cell and contribute to the high efficiency and high viability of transfection.

Accordingly, in various embodiments, the methods involve contacting cells (into which the agent(s) are to be delivered) with anisotropic magnetic particles in the presence of the agent to be delivered; applying a substantially uniform magnetic field to the magnetic particles where movement of said particles induced by said magnetic field introduces transient openings into the cell facilitating entry of the agent(s) of interest into the cells.

An anisotropic magnetic microparticle refers to "shape anisotropic" magnetization indicating that the magnetic materials do not need to be pre-magnetized in any specific orientation. However in certain embodiments, the method may be performed with particles that have a preference to be magnetized in certain crystal orientation. In certain embodiments the method may be performed with premagnetized micromagnetic particles, however in such instances, care may need to be taken to reduce the particles' tendency to stick to each other and not to load evenly on a plate.

Figure 2:
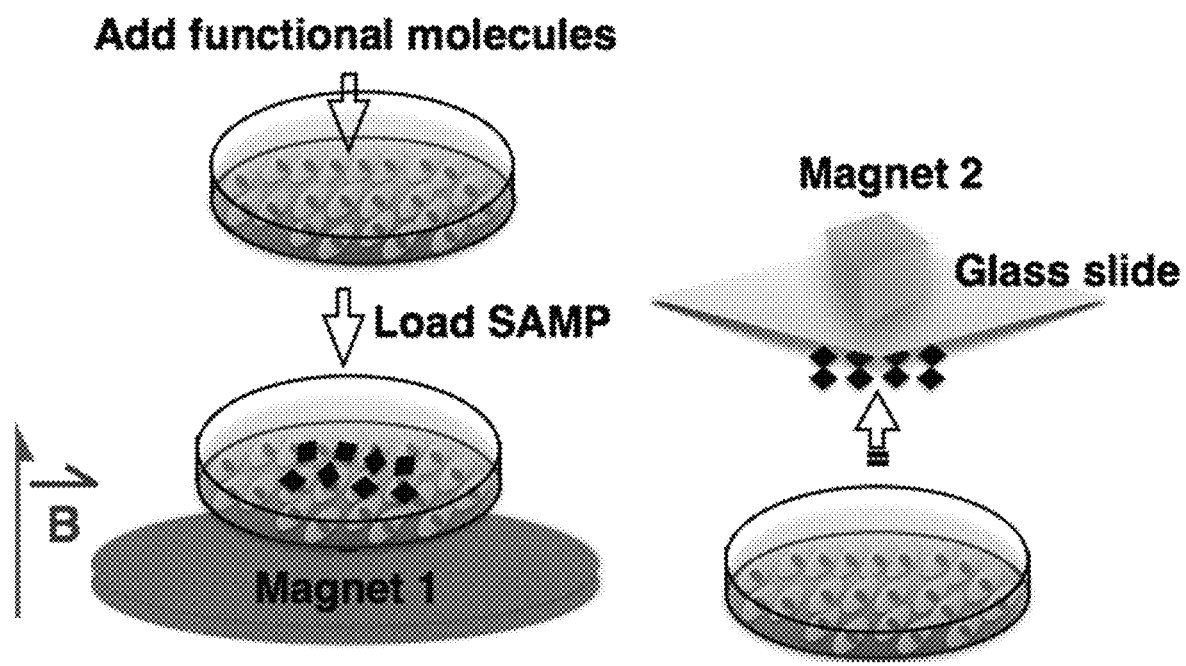
FIG. 2 schematically illustrates one embodiment of a procedure for intracellular delivery of functional molecules of interest using SAMPs. Functional molecules of interest are added into the cell culture dish, SAMPs loaded, SAMPs actuated with an external magnetic field, followed by removal of the SAMPs.

One illustrative embodiment of the method is schematically illustrated in FIG. 2. As illustrated therein the setup can includes a simple and easy to operate stage containing a cell culture dish and a bottom magnet for alignment of magnetic particles. In certain embodiments the distance between the cell culture dish and the magnet(s) can be adjustable for optimized delivery efficiency while in other embodiments the distance can be fixed. While the setup is illustrated with one magnet, in certain embodiments, multiple magnets can be utilized. Additionally, while a single culture dish is illustrated, in certain embodiments, vessels comprising multiple wells (e.g., microtiter plates) can also be utilized.

The agent(s) to be delivered into the cells are introduced into the medium in which the cells are disposed. The magnetic particles are then introduced into the same medium and the cells/medium are exposed to a uniform magnetic field (e.g., by disposing a magnet in proximity to the cells) for, e.g., from about 1, or from about 2, or from about 3, or from about 4 or from about 5 seconds up to about 30 seconds, or up to about 20 seconds, or up to about 15 seconds, or up to about 10 seconds. In certain embodiments the cells/medium are exposed to the magnetic field from about 1 second up to about 3 seconds or up to about 5 seconds. Movement/reorientation of the magnetic particles introduces lesions in the cell membrane permitting the agent(s) to be delivered to enter the cells. In certain embodiments, where desired, the magnetic particles can then be removed by the application of a magnetic field, e.g., by using a second magnet.

In one particular, illustrative, but non-limiting embodiment the method involves:

1) Adding the agent(s) to be delivered into the cells to cells in a culture dish;
2) Loading anisotropic magnetic microparticles into the same dish;
3) Place the dish on the a magnet (e.g., on the stage) to align magnetic microparticles, e.g., for 1-3 seconds;
4) Remove the dish and, optionally rest for, e.g., 10 mins at 25° C.; and
5) Optionally remove the microparticles using a magnet; and 6) Optionally rest, e.g., for 15 mins at 37° C.

Significant advances of this intracellular delivery method are that it is easy to operate, high throughput, high efficiency and maintains high cell viability. As illustrated in FIG. 2, the method can be run as a batch mode process. Each batch can take about 30 minutes or less to accomplish all delivery steps with a simple experimental design. In the illustrated setup, each batch can deliver materials into up to 40,000 cells. For high throughput delivery, magnetic particles can be pre-loaded in cell culture dishes. Each dish needs only less than 10 seconds on the magnetic stage to align the magnetic particles to scratch contacting cell membranes and create transient membrane pores for delivery. It is estimated that a throughput of 400,000 cells/min or higher can be achieved.

The method is simple and compatible with all kinds of cell culture dishes (e.g., microtiter plates and the lie). The method is also inexpensive. The micro-sized magnetic particles used in the examples described herein widely available commercially. For example, a kilogram (Kg) of Ni power is only about 10 dollars and can be used to deliver materials in thousands of dishes.

Additionally the method is easy to operate. In certain embodiments the micron sized magnetic particles can be simply sprinkled on cells in cell culture dishes. Alignment of the magnetic particles by a magnet can be performed in seconds. There is no additional fabrication of chips or nanometer-sized vectors (such as nanowires, nano-needles, or nanostraws). Compared to the state-of-the-art technologies, there is no conjugation of molecules onto the magnetic particles, which can increase the processing efficiency and decrease the amount of unconjugated molecules. Another noteworthy advantage of using micro-sized magnetic particles is that there is less cell toxicity compared to nanometer sized magnetic particles, because the micro-sized magnetic particles won't enter into the cells. Compared with electroporation technology for gene delivery, the methods described herein are completely culture dish compatible. There is no additional purchase of expensive electroporation delivery cuvettes and no recovery of adherent cells required during the process. This will contribute dramatically to cell survivability, due to no electronic shock, less processes, and experiments can be performed on the same dish that cells grow in following cargo delivery.

The prototype platform of the magnetic particle-based intracellular cell delivery has been achieved and tested. Three types of cells (HeLa cells, normal human dermal fibroblasts, and primary neurons) have been tested for delivery of molecules with various sizes of cargo (calcein dye, dextran 3 Kda and dextran 40 Kda). Moreover, we also evaluated the delivery efficiency and performed functional analyzes of functional molecules, including gene expression of green fluorescence protein (GFP), siRNA delivery, and coupled enzyme reactions using beta-lactamase delivery. Test data are provided in the Example.

Figure 10:
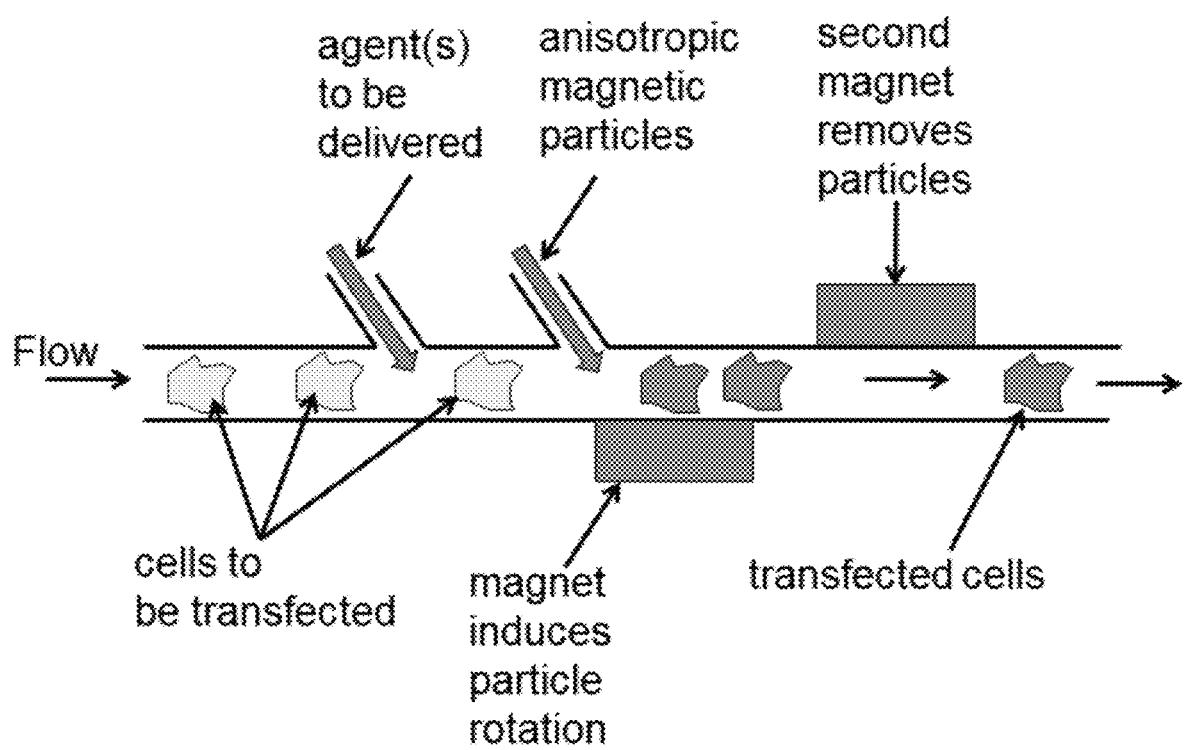
FIG. 10 schematically illustrates one embodiment of a flow-through transfection system using anisotropic magnetic particles.

It will be recognized that using the teaching provided herein delivery of cargo into cells using anisotropic magnetic particles can be achieve in formats other than the culture dish forma illustrated in FIG. 2. For example, a microfluidic flow-through approach of the method is schematically illustrated in FIG. 10. As shown therein, cells to be transfected are delivered in a flow path through a channel. The agents to be delivered can be introduced into that channel at a first location and the anisotropic magnetic particles can be introduced into the channel at a second location. Alternatively, the agent(s) to be delivered can be combined with the magnetic particles and the two can be delivered at one location. The cells then flow past a magnet that induces rotation/movement of the magnetic particles opening lesions in the cell membrane for entry of the agent(s). The magnetic particles are then removed from the cells downstream by a second magnet. Where the second magnetic is an electro magnet, the removed magnetic particles can subsequently be release and flushed out of the system. In certain embodiments the channel is of a dimension sufficient to partially restrict movement of the cells so that they don't substantially move in response to the action of the rotating magnetic particles.

Figure 11:
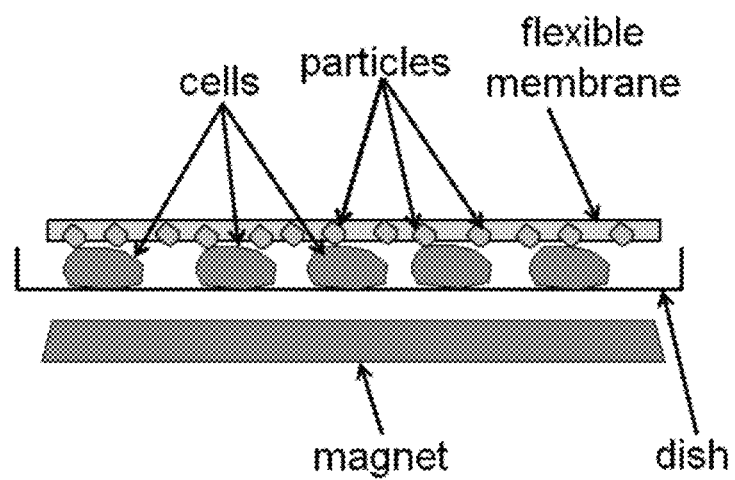
FIG. 11 schematically illustrates one embodiment that utilizes magnetic particles disposed on or near the surface of a flexible membrane.

Another illustrative, but non-limiting platform is schematically illustrated in FIG. 11. In this embodiment a layer of magnetic particles are disposed on or embedded at or near the surface pf a soft, elastic polymer membrane (e.g., PDMS). This membrane can be placed on top of cells in a petri dish. Applying a magnetic field can rotate the embedded microparticles to scratch cells in contact. After delivery, this membrane can be easily peeled off from the patri disk and reused.

Magnets useful in the method described herein include, but are not limited to neodymium magnets, samarium cobalt (SmCo) magnets, alnico magnets, and ceramic or ferrite magnets. In certain embodiments electromagnets can also be used and may well be suited to automated systems. In certain embodiments the magnet(s) range in size from about 0.5 inch in length or diameter up to about 6 inches in length or diameter. In certain embodiments the magnet has surface field strength that ranges from about 0.001 Tesla up to about 10 Tesla. In certain embodiments the magnet is disposed to provide a field strength at said cells ranging from about 0.01 tesla up to about 0.1 tesla.

Anisotropic magnetic particles useful in the methods described herein are widely available from commercial sources. In certain embodiments the anisotropic magnetic particles comprise a material selected from the group consisting of iron, nickel, cobalt, and alloys thereof. In certain embodiments the magnetic particles range in average or median size from about 20 µm, or from about 30 µm, or from about 40 µm, or from about 50 µm in diameter up to about 200 µm, or up to about 150 µm, or up to about 100 µm, or up to about 80 µm, or up to about 60 µm in diameter. In certain embodiments the magnetic particles are of a size that prevents internalization into said cells. In certain embodiments the magnetic particles are of a size that prevents internalization into said cells via endocytosis, or pinocytosis. In various embodiments the magnetic particles are sterile before application to said cells.

In various embodiments the cells that can be transfected using the methods described herein include, but are not limited to prokaryotic cells and eukaryotic cells. In certain embodiments the cells comprise mammalian cells (e.g., human cells or non-human mammalian cells). In certain embodiments the cells comprise cells selected from the group consisting of fibroblasts, neural cells (e.g., cortical neurons), A549 cells, HeLa cells CHO cells primary human mammary epithelial cells (HMEC), red blood cells, white blood cells (including B and T cells), and stem cells. In certain embodiments the cells comprise stem cells selected from the group consisting of fetal stem cells, adult stem cells, cord blood stem cells, and induced pluripotent stem cells. In certain embodiments the cells comprise stem cells derived from bone marrow or adipose tissue.

Any of a variety of agents can be delivered into cells using the methods described herein. In certain embodiments the agents comprise one or more agents selected from the group consisting of a nucleic acid and a protein or peptide. In certain embodiments the agents comprise one or more agents selected from the group consisting of an enzyme, a plasmid, a viral vector, a cosmid, an artificial chromosome, an antibody, an RNAi, and components of a CRISPR/Cas9 system (e.g., Cas9, and/or crRNA, and/or trRNA). In certain embodiments the agents comprise CRISPR/Cas9 variants or alternatives. Thus, for example, in certain embodiments the agents comprise Cas9 from *Streptococcus pyogenes* (SpCas9) or a nucleic acid encoding, inter alia Cas9 from *Streptococcus pyogenes* (SpCas9). In certain embodiments the agents comprise Cas9 from *Streptococcus aureus* (SaCas9) or a nucleic acid encoding, inter alia, Cas9 from *Streptococcus aureus* (SaCas9). In certain embodiments the agents comprise a vector (e.g., an AAV vector or lentiviral vector) encoding a Cas9 (e.g., SpCas9, SaCas9, etc.) and a single guide RNA or two guide RNAs. In certain embodiments the agents comprise a Cpf1 nuclease (e.g., from *Acidaminococcus* sp. BV3L6 (AsCpf1), or from *Lachnospiraceae bacterium* ND2006 (LbCpf1), see, e.g., Kleinstiver et al. (2016) *Nat. Biotechnol.* 34: 869-874), or a nucleic acid encoding the Cpf1. In certain embodiments the agents comprise a vector (e.g., an AAV vector or lentiviral vector) encoding a Cpf1 (e.g., AsCpf1, LbCpf1) and a single guide RNA.

In certain embodiments kits are provided for performing the methods described herein. In certain embodiments the kit comprises a container containing anisotropic magnetic particles; and a magnet (e.g., a magnet that has a substantially uniform magnetic field sufficient to induce movement of said particles and to introduce transient openings into a cell in contact with said particles and to facilitating entry of an agent of interest into said cell). In certain embodiments the kit comprises a cell culture vessel containing anisotropic magnetic particles, where the cell culture vessel provides an aliquot of said magnetic particles containing sufficient particles for a single transfection procedure. In certain embodiments the kit comprises a plurality of containers each containing anisotropic magnetic particles, wherein each container provides an aliquot of said magnetic particles sufficient for a single transfection procedure. In certain embodiments each container (or cell culture vessel) provides sufficient magnetic particles to apply said particles to said cells at a density ranging from about $2 \times 10^4$ particles/cm, or from about $4 \times 10^4$ particles/cm, or from about $6 \times 10^4$ particles/cm up to about $20 \times 10^4$ particles/cm, or up to about $15 \times 10^4$ particles/cm, or up to about $10 \times 10^4$ particles/cm. In certain embodiments the kit further comprises a magnet that provides a substantially uniform magnetic field sufficient to induce movement of said particles and to introduce transient openings into a cell in contact with said particles and to facilitating entry of an agent of interest into said cell.

In certain embodiments the kit further contains labeling and/or instructional materials teaching a transfection method described herein. Thus, for example, the instructional materials provide protocols for the use of the anisotropic magnetic particles to introduce agents into cells of interest.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Intracellular Delivery by Shape Anisotropic Magnetic Particle-Induced Cell Membrane Cuts Introducing functional macromolecules into a variety of living cells is challenging but important for biology research and cell-based therapies. We report a novel cell delivery platform based on rotating shape-anisotropic magnetic particles (SAMPs), which make very small cuts on cell membranes for macromolecule delivery with high efficiency and high survivability. SAMP delivery is performed by placing commercially available nickel powder onto cells grown in standard cell culture dishes. Application of a uniform magnetic field causes the magnetic particles to rotate because of mechanical torques induced by shape-anisotropic magnetization. Cells touching these rotating particles are nicked which generates transient membrane pores that enable the delivery of macromolecules into the cytosol of cells. Calcein dye, 3 and 40 kDa dextran polymers, a GFP plasmid, siRNA, and an enzyme (β-lactamase) were successfully delivered into HeLa cells, primary human dermal fibroblasts (NHDFs), and mouse cortical neurons that can be difficult to transfect. The SAMP approach offers several advantages including easy implementation, low cost, high throughput, and efficient delivery of a broad range of macromolecules. Collectively SAMP delivery has great potential for a broad range of academic and industrial applications.

Methods and Procedures

SAMP

Figure 1:
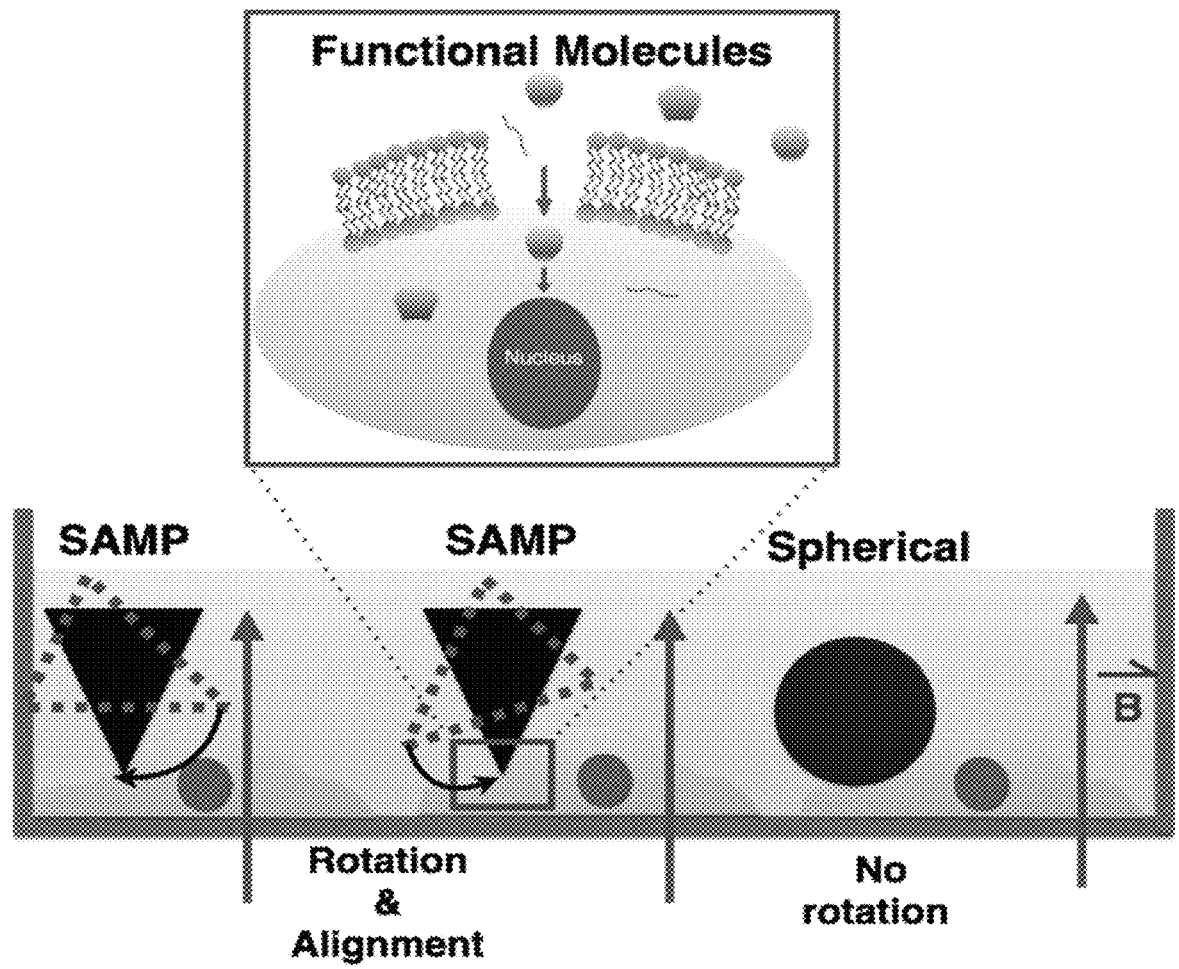
FIG. 1 schematically illustrates the principle of intracellular delivery using the shape-anisotropic magnetic particle (SAMP) method. A uniform magnetic field magnetizes SAMPs and aligns their axes with the applied field. Cells touching SAMPs are scratched and open transient membrane pores for cytosolic delivery. Magnetic particles with symmetrical structural shapes (e.g., spherical shapes) do not rotate under a uniform magnetic field since there is no directional preference of magnetization. Each magnetized particle is a new magnetic dipole that can induce particle-particle interactions to trigger local migration and form particle chains, which also can induce scratches on cells along the particle migration paths.

The working principle of SAMP is based on rotating shape anisotropic magnetic particles under a uniform magnetic field. Cells touching rotating magnetic particles are scratched to generate transient membrane cuts or pores for delivery. There are two unique features and major advantages of the SAMP method. First, shape anisotropic magnetization and particle rotation can be induced by a uniform magnetic field as shown in FIG. 1. This feature provides a major advantage over conventional transfection based on micro or nanoparticle manipulation, in which a non-uniform magnetic field is required to create a field gradient to produce magnetic forces that translate micro or nano magnetic particles. Generating a constant magnetic force on magnetic particles across a large area requires the creation of a uniform "gradient" of magnetic fields across a large area, which is very difficult to achieve. In SAMP, only a uniform magnetic field is required. Cell membrane opening is realized by rotating magnetic microparticles that scratch and cut contacting cells. When magnetic particles with anisotropic shapes are used, their magnetization axes will automatically align with an external magnetic field. Of note is that each of these magnetized particles is also a magnetic dipole. Magnetic dipoles can attract each other to induce local particle migration. Local particle migrations induced by particle-particle interactions, in addition to particle rotation, can also scratch and cut cell membranes. The requirement of a uniform external field in SAMP is unique, especially for delivery across a large area (>few $cm^2$) since a uniform magnetic field can be easily obtained with widely available disc-shape magnets. A second major advantage is that the SAMP approach does not require any microfabrication steps. All materials and components used in SAMP can be easily obtained at low cost. Also, there is no need for chemical modification of the magnetic particles since SAMP is a purely physical approach for cell membrane opening.

For SAMP delivery, the molecules of interest to be delivered were first added into the cell culture medium. Then, SAMPs were dispersed randomly and evenly onto cells at a density of 6-9×10$^4$ particles/cm$^2$. The culture dish was quickly placed above a disc-shaped magnet (magnet 1) for 1 sec at a distance of 3-5 cm and moved away (FIG. 2). Magnetic field strengths were 0.039 Tesla at distance of 3 cm and 0.020 Tesla at the distance of 5 cm. After 10 seconds of incubation at room temperature, the SAMPs were removed from the cells by another magnet (magnet 2) placed above the cultured dish. The cells were incubated with the molecules of interest for 15 minutes at 37° C., washed three times with 1×PBS, pH7.4, and placed back into their culture medium.

Of note is that the 40-60 μm in diameter magnetic particles used in SAMP helps to avoid cell engulfment by endocytosis, pinocytosis, or other mechanisms. Failed cell engulfment also prevents known particle cytotoxicity for nanomagnetic particles that are taken into cells in this way (Singh et al. (2013) *Toxicol. Appl. Pharmacol.*, 266(1): 56-66; Colombo et al. (2012) *Chem. Soc. Rev.* 41(11): 4306-4334).

Magnetic Field Distribution

Figure 3:
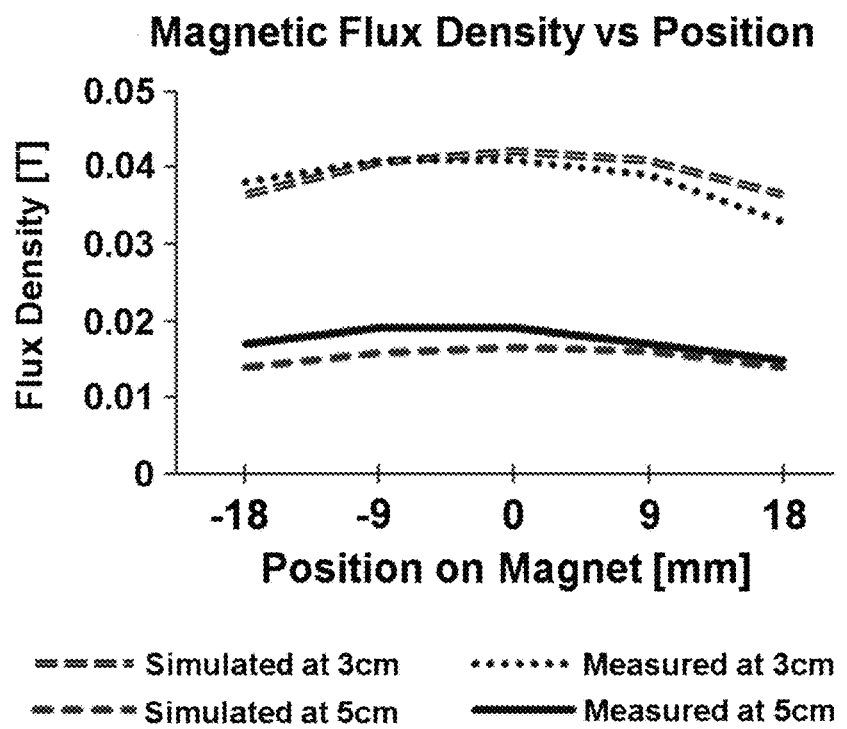
FIG. 3 shows measured normal components of the magnetic flux density distribution across the disc magnet used for the SAMP method at 3 and 5 cm above disc surface. The magnet's center is located at position 0 mm.

Experimental measurements of the magnetic flux density of the disc magnet was compared to the theoretical results simulated by COMSOL. The magnet is a N42 graded neodymium disc (Stanford Magnets Co.) and is composed of NdFeB and is 3" in diameter and ¼" in thickness; its surface field strength is approximately 1085 Gauss. FIG. 3 compares the measured values of the normal component of magnetic flux density to those of the simulation across the magnet's surface at distances of 3 and 5 cm. A Hall probe was positioned in parallel to the surface for each measurement; thus, only the normal components of the flux were obtained.

Figure 4A:
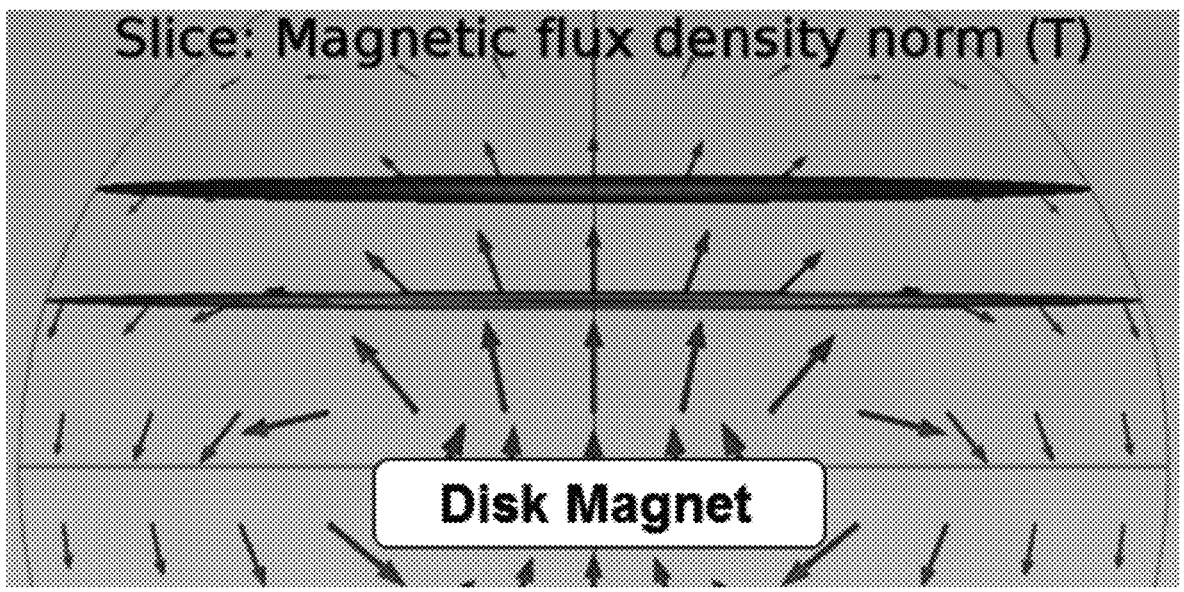
FIGS. 4A-4C illustrate numerically simulated magnetic flux density and field direction.
Figure 4B:
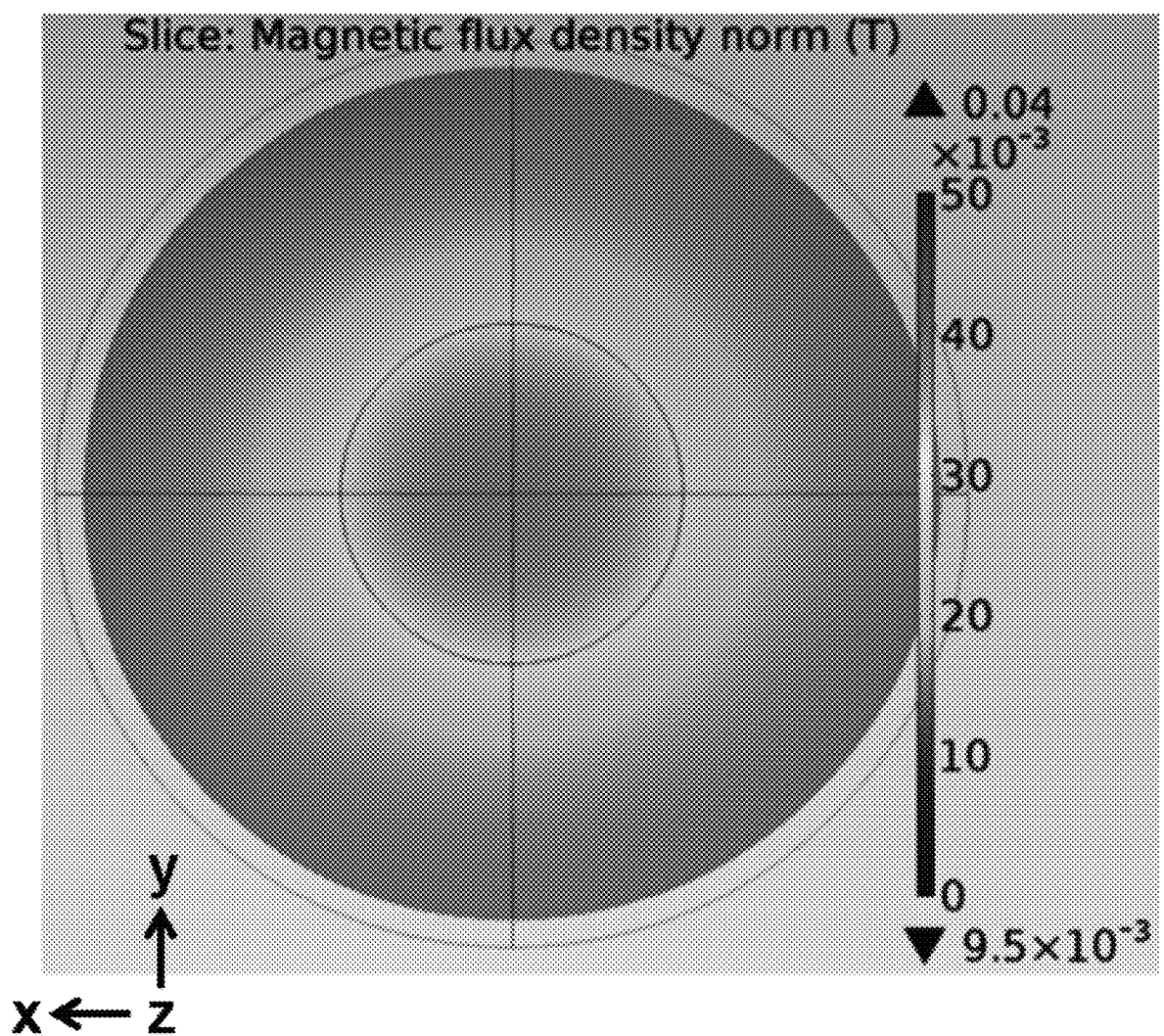
Figure 4C:
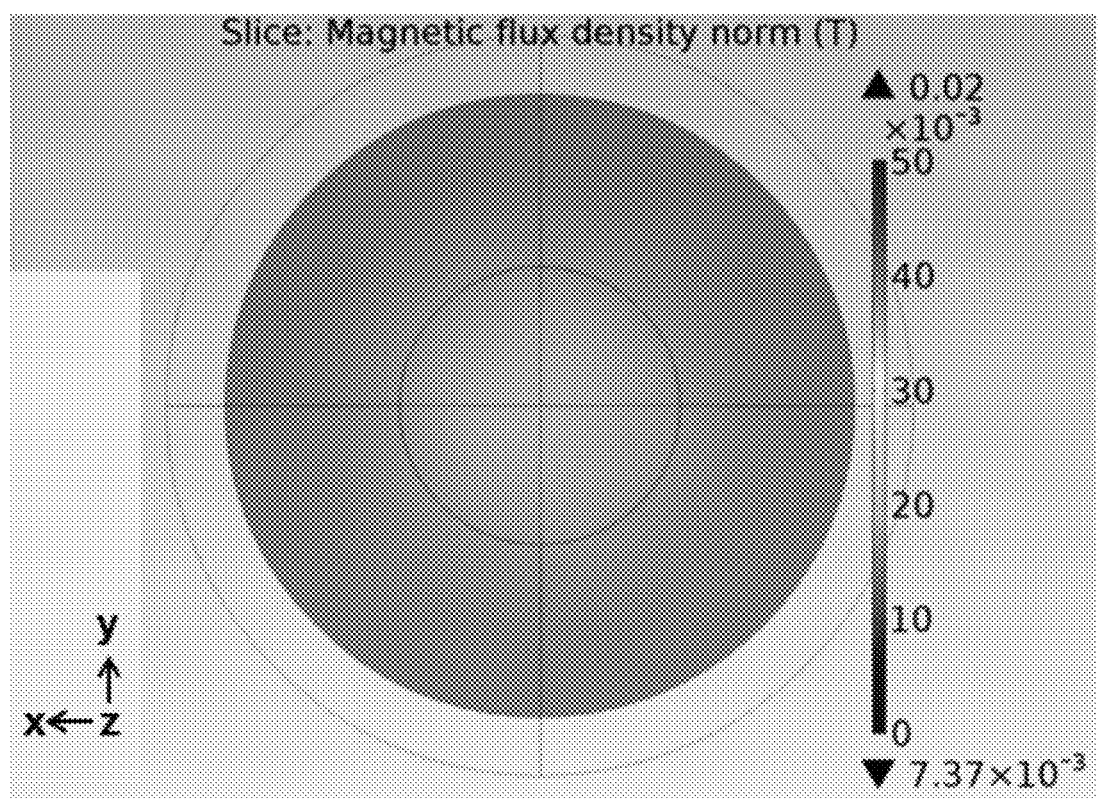

FIGS. 4A-4C illustrate the numerically simulated, corresponding magnetic field directions and flux densities at 3 and 5 cm away from the disc surface, respectively. Both the simulation and experimental results show that the magnetic field strength around the center of the magnet disc is uniform and the field direction is perpendicular to the disk. For optimal SAMP delivery, micro magnetic particles are sprinkled near the center location where magnetic field is uniform. When magnetic particles are sprinkled at locations near the edge of the magnet disk, a strong magnetic field gradient will induce large magnetic forces on the particles to induce fast migration, which damages cells immediately.

Cell Culture

HeLa cells were maintained in Dulbecco's modified eagle medium (DMEM, Corning) supplemented with 10% fetal bovine serum (FBS, Corning), 4.5 g/L glucose, L-glutamine, sodium pyruvate and penicillin/streptomycin. NHDFs (Lonza) were cultured in Fibroblast Basal Medium with hFGF-B, insulin, FBS and gentamicin/amphotericin-B (Corning). Mouse cortical neurons were prepared from C57BL/6J mice (Jackson Laboratory) on postnatal day 0 as previously described (Ho et al. (2014) *Mol Cell Neurosci.*, 61: 1-12) and cultured in Neurobasal-A media (Life Technologies) supplemented with 1×B27 supplement (Life Technologies), 0.25× GlutaMAX supplement (Life Technologies), 25 μM glutamate (Sigma-Aldrich), and 25 μM β-mercaptoethanol (Sigma-Aldrich). Before delivery, HeLa and NHDF cells were seeded in 35 mm petri dishes. Neurons were grown in 24-well multi-well plates.

Sterilization of Magnetic Particles

Magnetic particle sterilization was by treatment of 500 mg nickel metal powder (99.9% pure, Atlantic Equipment Engineers, 40-60 μm in diameter) with 1 ml of 75% ethanol for 30 mins. 1× phosphate-buffered saline (PBS, pH 7.4, Corning) was used to wash SAMPs four times, and the SAMPs were resuspended in 1 ml 1×PBS, pH 7.4. SAMPs were stored in aliquots at 100 mg/ml in 1×PBS, pH 7.4.

Evaluation of Delivery Efficiency and Cell Viability

The delivery efficiency was calculated as the number of cells with delivered materials divided by the total number of cells. Cell viability was checked by propidium iodide (PI) staining (5 μg/ml, Invitrogen) or, in some cases, DAPI staining (1 μg/ml, Invitrogen). PI was added to cells 10 min after the application of SAMPs and the magnetic field, incubated for 5 min, and removed. Cell viability was calculated as the number of cells without PI or DAPI staining divided by the total number of cells×100. Fluorescence images of intracellular delivery of calcein dye and dextran particles (3 and 40 kDa), green fluorescence protein expression, and a β-lactamase activity assay in cells were obtained by using an inverted fluorescence microscope (Axio Observer.D1m, Carl Zeiss) with 10× and 40× objective lenses. Expression of lamin A/C to evaluate the efficacy of lamin A/C siRNA was also performed by immunofluorescence staining and recorded using an inverted fluorescence microscope (IX70, Olympus).

Results and Discussion

Efficiency and Cell Viability for SAMP-Delivered Molecules of Different Sizes

Figure 5:
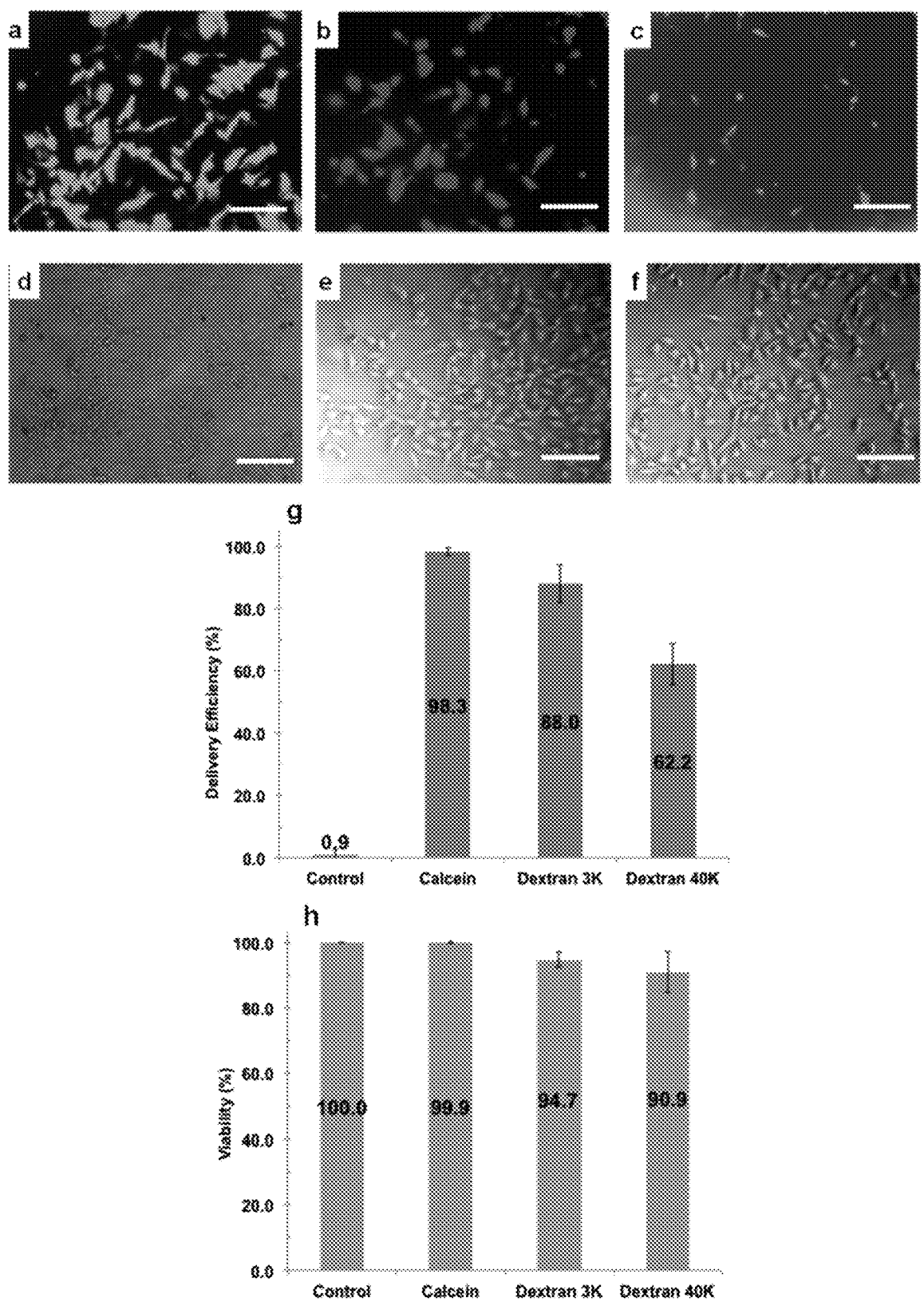
FIG. 5, panels a-c, show fluorescence images of HeLa cells delivered with calcein dye (0.1 mg/ml, Invitrogen) (panel a), dextran 3K (1 mg/ml, tetramethylrhodamine-labeled dextran 3 KDa, Invitrogen) (panel b), and dextran 40K (1 mg/ml, fluorescein-labeled dextran 40 KDa, Invitrogen) with SAMP treatment (panel c).
Figure 6:
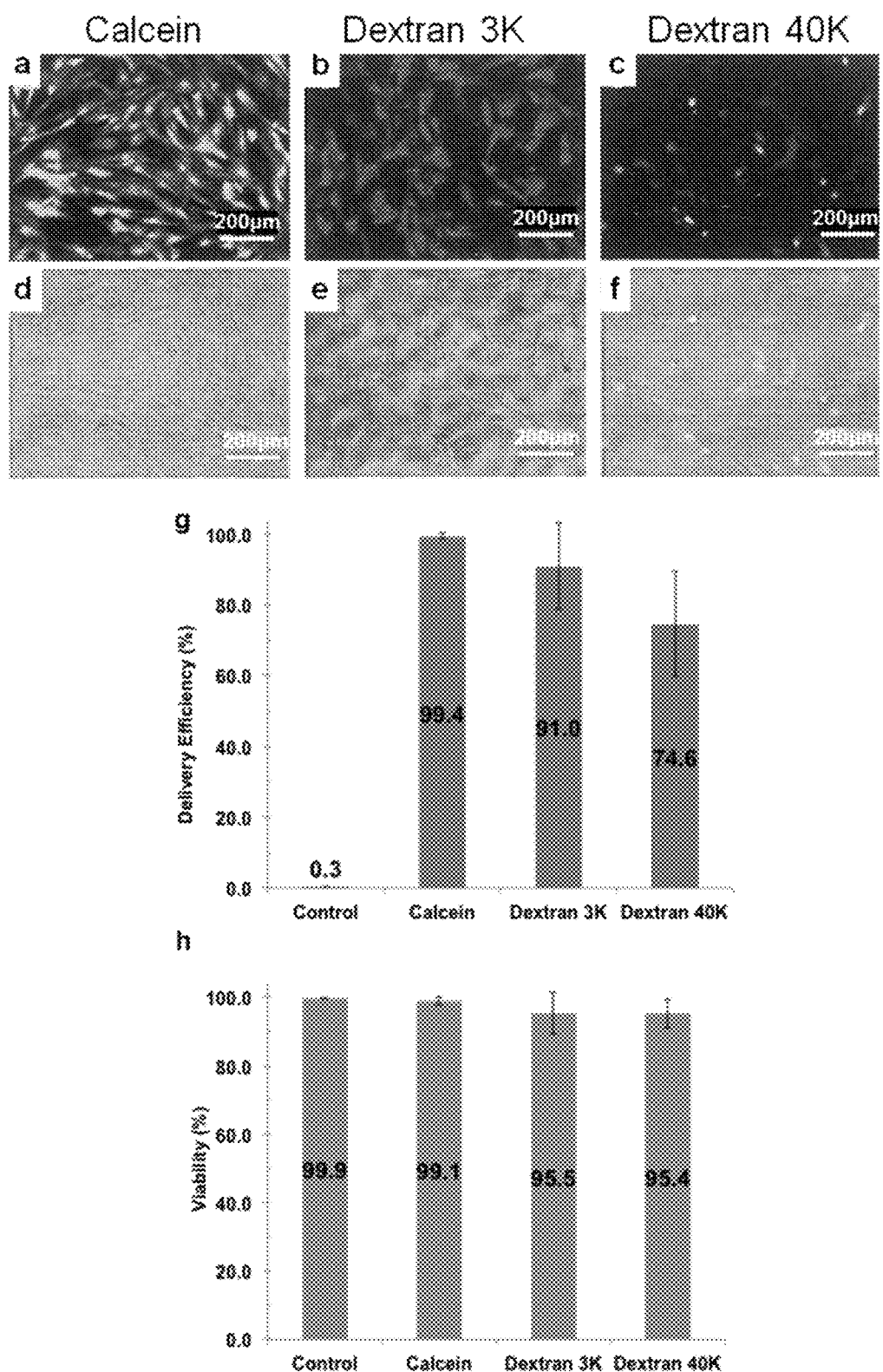
FIG. 6, panels a-c, show fluorescence images of NHDF cells after SAMP delivery of calcein dye (0.1 mg/ml), dextran 3K (1 mg/ml), and dextran 40K (1 mg/ml).

To evaluate the SAMP method three different sizes of membrane-impermeable molecules, including calcein dye (623 Da) and dextran particles (3 and 40 kDa), were delivered into HeLa cells, NHDFs and mouse cortical neuron cells. In HeLa cells, the delivery efficiency of calcein dye and 3 kDa and 40 kDa dextran particles was 98.3%, 88.0%, 62.2%, respectively (FIG. 5). The delivery efficiency decreased as cargo size increased, consistent with a mechanism in which transient membrane pores start to reseal after being scratched and cut, with larger cargo having less time to pass through membrane pores by diffusion before they close. Similar trends were recorded for cargo delivery into NHDFs, in which the delivery efficiencies observed were 99.4%, 91.0%, 74.6%, respectively (FIG. 6). Cell viability for both HeLa and NHDF cells post cargo delivery was >90% in all experiments.

Figure 7:
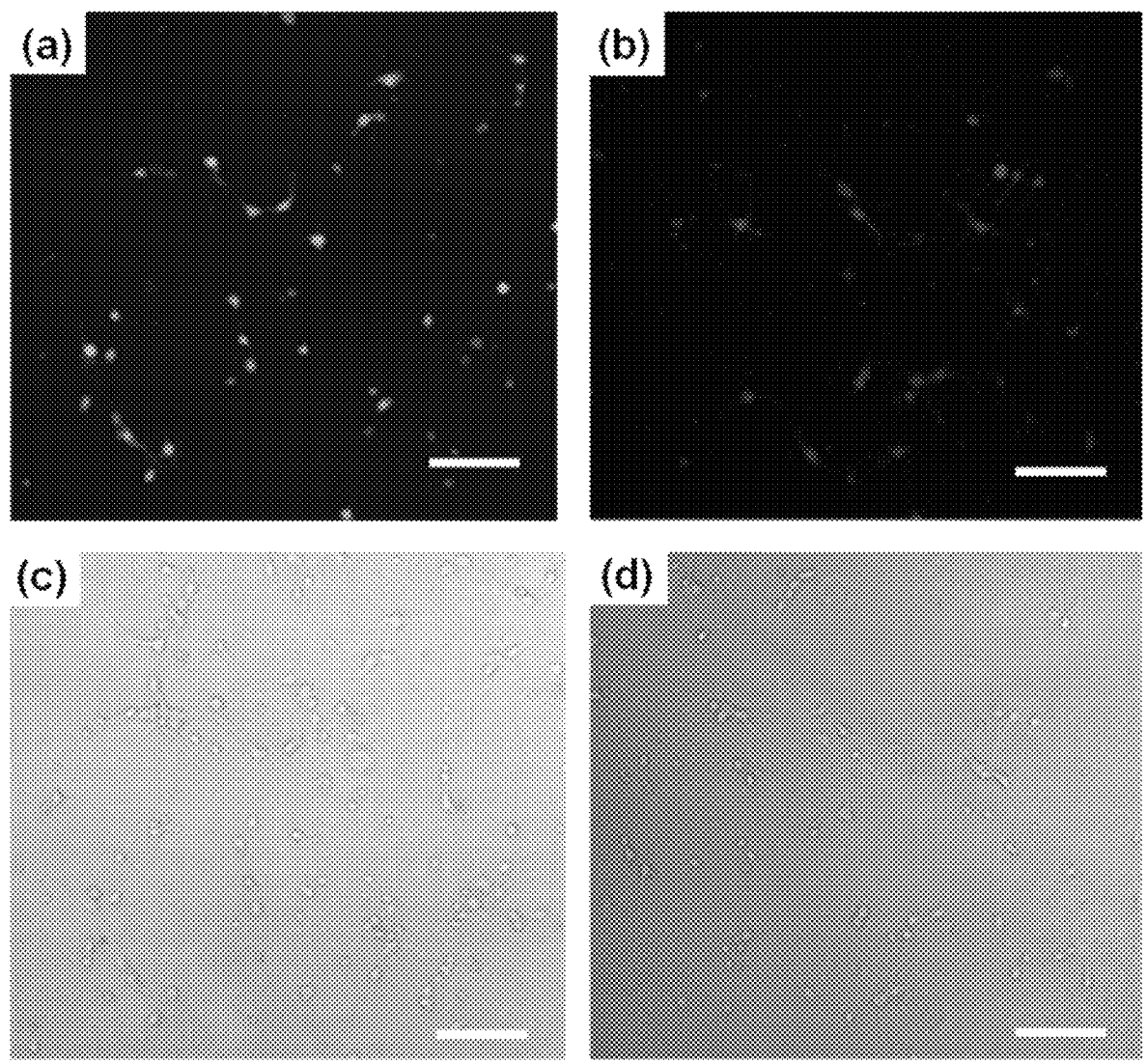
FIG. 7, panels a, c, show fluorescence and bright field images of mouse cortical neurons (9 days in vitro, DIV) delivered with calcein dye (0.1 mg/ml).

Intracellular delivery of macromolecules into post-mitotic cells currently remains challenging. Therefore, we tested SAMP delivery efficiency in primary cultured neurons that are post-mitotic. Using the SAMP method, calcein dye was delivered into 44.4% of mouse cortical neurons that were cultured 3 days in vitro (DIV) after preparation from mouse brain at postnatal day 0, and 3 kDa dextran was delivered into 40.2% of neurons at the same age (FIG. 7). Similar delivery efficiencies of 54.2% for calcein dye and 42.5% for 3 kDa dextran particles were achieved for more mature neurons at age of DIV 9. Moreover, >97% cell viability was recorded for neurons at both ages post-SAMP delivery (FIG. 7, panel e).

Delivery of Plasmids and siRNAs

Figure 8:
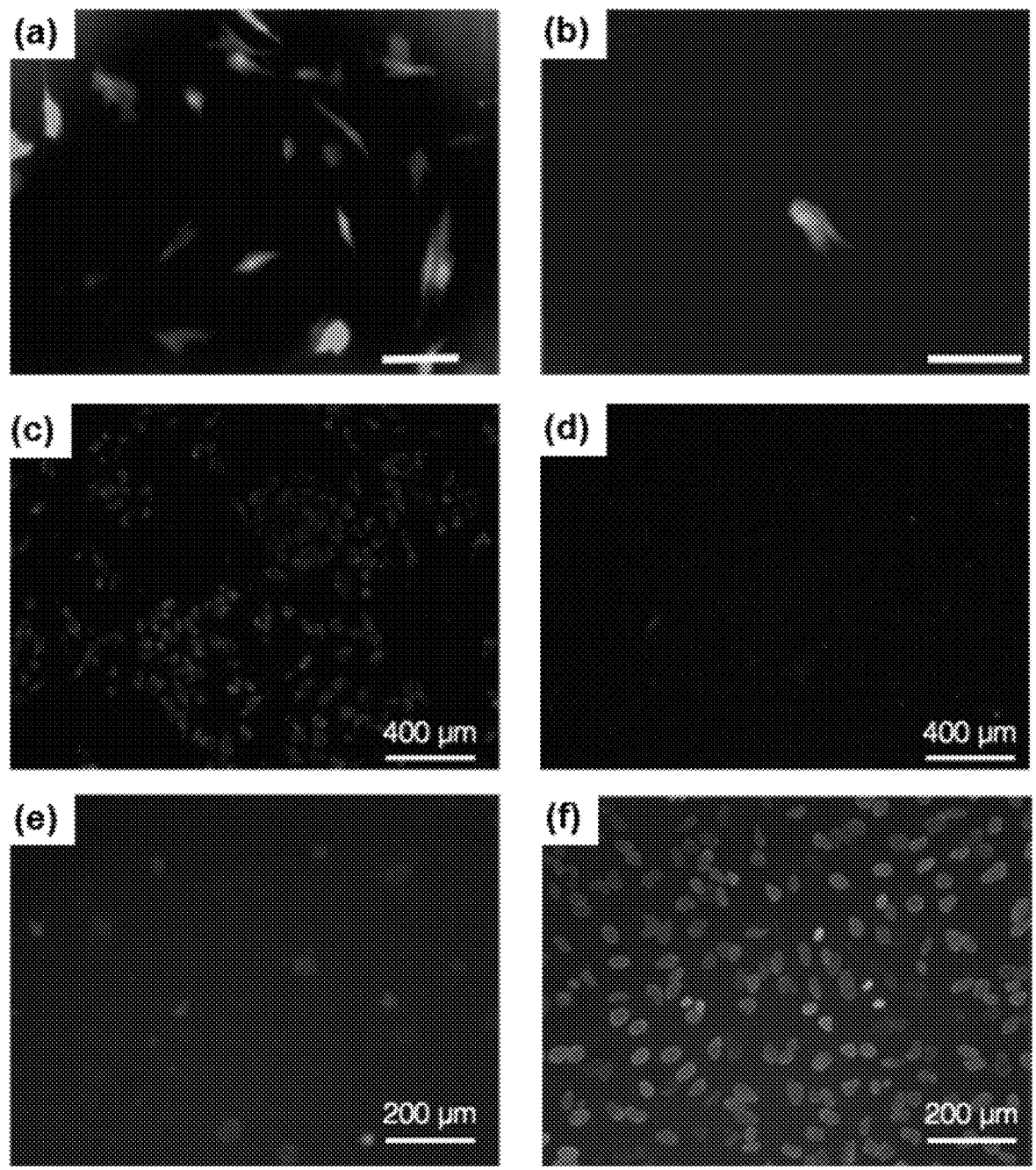
FIG. 8, panels a-h, illustrates intracellular delivery of functional nucleic acid molecules: GFP plasmids and siRNA.

We delivered a liposome-coated GFP-expression plasmid (pEGFP-N1, 4.7 Kb) using SAMP. Approximately 72.2% of NHDF cells expressed GFP 48 hours after delivery on the SAMP platform. This efficiency is a five-fold higher efficiency than NHDF cell delivery by liposome encapsulation only (13.3%) (FIG. 8, panels a-b, g). Protein expression from introduced plasmid DNA using lipofection techniques is typically low, with significant cytotoxicity in many primary cell types (Movahedi et al. (2015) *Nanomedicine: NBM*, 11(6): 1575-1584; Chen et al. (2003) *Clin. Exp. Dermatol.*, 28(2): 193-199). Therefore, the SAMP platform could facilitate the delivery of functional plasmids into primary cells.

Variable efficiencies for intracellular delivery of siRNAs into different cell types have been reported (Dalby et al. (2004) *Methods*, 33(2): 95-103). Therefore, a method for efficient delivery of siRNAs into cells would be important for basic studies and possibly translational applications. With SAMP, 95.4% of HeLa cells were transduced by lipofectamine encapsulated siRNA against lamin A/C. A reduction of lamin A/C protein from 90.6% to 7.0% was observed by immunocytochemistry, validating SAMP delivery of siRNA into HeLa cells (FIG. 8, panels c-f, h).

Delivery of β-Lactamase and Enzyme Cascade Reaction

Figure 9:
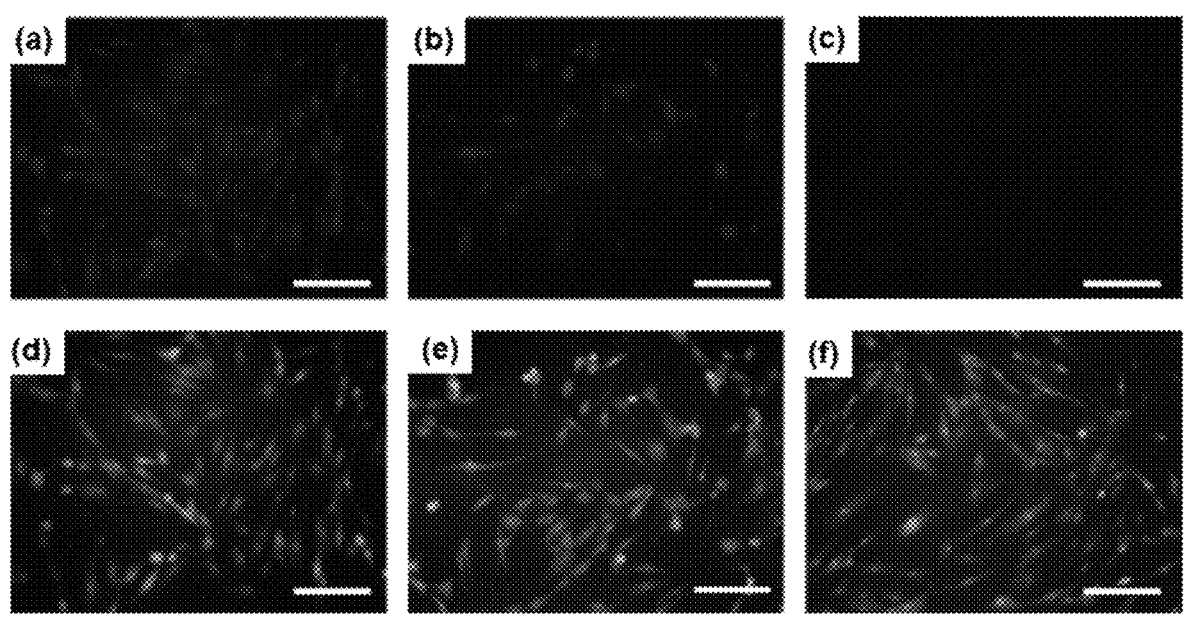
FIG. 9, panels a-h, illustrates that SAMP delivered β-lactamase enzyme shows catalytic function in NHDF cells.

Enzyme therapeutics is a promising and growing field in medicine because of catalytic activity and specificity of the approach. Protein and enzyme deliveries are challenging with other platforms due to the large size of the delivered cargo and the need to preserve functions post-delivery. The bacterial enzyme β-lactamase was delivered by SAMP into NHDF cells and delivery efficiency and functionality assessed by incubation with the membrane-permeant substrate CCF4-AM, a lipophilic, esterified form of the CCF4 substrate which allows it to readily enter cells, in post-delivery NHDF cells. CCF4-AM is naturally converted into CCF4 by endogenous esterases and retain in the cytosol in NHDFs. CCF4 is a fluorescence resonance energy transfer (FRET) substrate which consists of a cephalosporin core linking 7-hydroxycoumarin to fluorescein. In the absence of β-lactamase activity, emission of a green fluorescence signal at 530 nm from CCF4 is observed by FRET with excitation at 408 nm (FIG. 9, panels a-c). In the presence of exogenous β-lactamase activity, cleavage of CCF4 disrupts FRET, resulting in emission of a blue fluorescence signal at 460 nm. We observed that delivery of β-lactamase (10 units/ml or 50 units/ml) into NHDF cells resulted in the conversion of a green fluorescence signal to blue fluorescence (FIG. 9, panels d-f). Cells placed at 3 cm (stronger magnetic field) above the magnet show a higher delivery efficiency than at 5 cm (weaker magnetic field) and in both cases showed high cell viability >98% after SAMP treatment. Three concentrations of β-lactamase (10 IU/ml, 50 IU/ml, and 100 IU/ml) were SAMP delivered for comparison. The highest delivery efficiency, 89.9%, was achieved at a concentration of 100 IU/ml (FIG. 9, panel h). These results indicate that SAMP delivery of the exogenous β-lactamase into NHDFs is highly efficient with the catalytic enzyme activity maintained.

CONCLUSIONS

We have demonstrated an easy-to-use, low cost, and high throughput SAMP method for high efficiency intracellular delivery. SAMP delivery is purely physical and less cell type dependent. It is realized by rotating micron-sized, anisotropic-shaped, magnetic particles that scratch and induce cell membrane cuts for cargo to pass through into the cytosol. SAMP provides a batch mode delivery approach and each batch can deliver cargo into ~40,000 cells in 10 seconds in the current proof-of-concept demonstration. The throughput is linearly proportional to the area of a uniform magnetic field created by the magnet. Higher throughput up to a few million cells per batch can potentially be achieved by using a larger size disc magnet. Through properly controlled magnetic particle density, size, and magnetic field strength, SAMP delivery provides high cell viability and high efficiency delivery of a wide range of small and medium sized molecules, including calcein dye, 3 and 40 kDa dextran particles, a GFP plasmid, an siRNA, and an enzyme (β-lactamase) into multiple cell types including post-mitotic mouse cortical neurons. The SAMP delivery approaches were optimized for adherent cells. Cell adhesion to a substrate provides an anchoring balance force to allow membrane cuts to form during the particle scratching process.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of delivering an agent of interest into cells, said method comprising:
   providing a plurality of cells in a cell culture medium containing said agent;
   introducing shape-anisotropic magnetic particles that are not conjugated to said agent into said culture medium; and
   applying a substantially uniform magnetic field to said magnetic particles where movement of said particles induced by said magnetic field introduces transient openings into said cell facilitating entry of said agent of interest into said cells.

2. The method of claim 1, wherein said substantially uniform magnetic field is created by one or more magnets disposed in proximity to said cells.

3. The method of claim 2, wherein said magnet comprises a magnet selected from the group consisting of a neodymium magnet, a samarium cobalt (SmCo) magnet, an alnico magnet, and a ceramic or ferrite magnet.

4. The method of claim 2, wherein said cells are disposed in a vessel and said applying a substantially uniform magnetic field comprises disposing said vessel over said magnet.

5. The method of claim 2, wherein said magnet is disposed to provide a field strength at said cells ranging from about 0.01 tesla up to about 0.1 tesla.

6. The method of claim 1, wherein said substantially uniform magnetic field is created by an electromagnet.

7. The method of claim 1, wherein said cells are disposed in a vessel and said applying a substantially uniform magnetic field comprises placing said vessel over a disc-shaped magnet.

8. The method of claim 1, wherein said substantially uniform magnetic field is applied for a period of time ranging from about 0.5 sec up to about 30 sec.

9. The method of claim 1, wherein said method further comprises using a magnet to remove the magnetic particles from the medium in which the cells are disposed.

10. The method of claim 1, wherein said shape-anisotropic magnetic particles comprise a material selected from the group consisting of nickel, and cobalt, and alloys thereof.

11. The method of claim 1, wherein said shape-anisotropic magnetic particles range in average or median size from about 40 μm up to about 200 μm.

12. The method of claim 1, wherein said magnetic particles are of a size that prevents internalization into said cells.

13. The method of claim 1, wherein said magnetic particles are sterile before application to said cells.

14. The method of claim 1, wherein said magnetic particles are disposed in a flexible membrane that is applied to said cells.

15. The method of claim 14, wherein said flexible membrane comprises PDMS or another material used in soft lithography.

16. The method of claim 1, wherein said magnetic particles are applied to said cells at a density ranging from about $1 \times 10^3$ particles/cm up to about $3 \times 10^6$ particles/cm.

17. The method of claim 1, wherein said agent of interest comprises an agent selected from the group consisting of a nucleic acid, and a protein or a peptide.

18. The method of claim 1, wherein said agent of interest is selected from the group consisting of Cas9 from *Streptococcus pyogenes* (SpCas9), a nucleic acid encoding Cas9 from *Streptococcus pyogenes* (SpCas9), Cas9 from *Streptococcus aureus* (SaCas9), a nucleic acid encoding, Cas9 from *Streptococcus aureus* (SaCas9), a Cpf1 nuclease, a nucleic acid encoding the Cpf1 nuclease, and a guide RNA.

19. The method of claim 1, wherein said cells are prokaryotic cells.

20. The method of claim 1, wherein said cells comprise eukaryotic cells.

21. The method of claim 20, wherein said cells comprise mammalian cells.

22. The method of claim 21, wherein said cells comprises human cells.

23. The method of claim 20, wherein said cells comprise stem cells selected from the group consisting of fetal stem cells, adult stem cells, cord blood stem cells, and induced pluripotent stem cells.

24. The method of claim 1, wherein said method is configured for a high throughput format.

25. The method of claim 24, wherein said method is configured to perform at least 2, or at least 4, or at least 8, or at least 16, or at least 32, or at least 64, or at least 128 different transfections simultaneously.

26. The method of claim 1, wherein:
said substantially uniform magnetic field is not provided by a component of a magnetic stirrer; and/or
said substantially uniform magnetic field is not provided as an element of a magnetic cell isolation or cell component isolation.

27. The method of claim 22, wherein said cells comprise cells selected from the group consisting of fibroblasts, neural cells, A549 cells, HeLa cells, primary human mammary epithelial cells (HMECs), red blood cells, white blood cells, and stem cells.

28. The method of claim 1, wherein said agent of interest comprises one or more agents selected from the group consisting of an enzyme, a plasmid, a viral vector, a cosmid, an artificial chromosome, an antibody, an RNAi, a component of a CRISPR/Cas9 system, a color dye, and calcium.

* * * * *